United States Patent
Kohane et al.

(10) Patent No.: US 11,559,586 B2
(45) Date of Patent: Jan. 24, 2023

(54) NANOPARTICLES FOR TREATMENT OF CHOROIDAL NEOVASCULARIZATION AND OTHER INDICATIONS

(71) Applicant: Children's Medical Center Corporation, Boston, MA (US)

(72) Inventors: Daniel S. Kohane, Newton, MA (US); Yanfei Wang, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 17/057,630

(22) PCT Filed: May 21, 2019

(86) PCT No.: PCT/US2019/033314
§ 371 (c)(1),
(2) Date: Nov. 20, 2020

(87) PCT Pub. No.: WO2019/226651
PCT Pub. Date: Nov. 28, 2019

(65) Prior Publication Data
US 2021/0236652 A1     Aug. 5, 2021

Related U.S. Application Data

(60) Provisional application No. 62/675,026, filed on May 22, 2018.

(51) Int. Cl.
| | |
|---|---|
| *A61K 47/69* | (2017.01) |
| *A61K 47/62* | (2017.01) |
| *A61K 47/68* | (2017.01) |
| *A61P 27/02* | (2006.01) |
| *A61K 31/704* | (2006.01) |
| *A61K 41/00* | (2020.01) |

(52) U.S. Cl.
CPC ........ *A61K 47/6937* (2017.08); *A61K 31/704* (2013.01); *A61K 41/0042* (2013.01); *A61K 47/62* (2017.08); *A61K 47/68* (2017.08); *A61P 27/02* (2018.01)

(58) Field of Classification Search
CPC ............ A61K 47/6937; A61K 41/0042; A61K 47/68; A61K 9/51
See application file for complete search history.

(56) References Cited

U.S. PATENT DOCUMENTS

2014/0342992 A1* 11/2014 Gait ................ A61P 35/00
                                                514/17.7
2018/0311353 A1   11/2018 Kohane et al.

FOREIGN PATENT DOCUMENTS

| WO | WO 2011/151814 A2 | 12/2011 |
|---|---|---|
| WO | WO 2014/117203 | 8/2014 |
| WO | WO 2015/059180 A2 | 4/2015 |
| WO | WO 2017/004310 | 1/2017 |

OTHER PUBLICATIONS

European Office Action dated Dec. 3, 2018 for Application No. EP 16818746.6.
Extended European Search Report dated Mar. 28, 2019 for Application No. EP 16818746.6.
International Search Report and Written Opinion dated Oct. 13, 2016 for Application No. PCT/US2016/040271.
International Preliminary Report on Patentability dated Jan. 11, 2018 for Application No. PCT/US2016/040271.
International Search Report and Written Opinion for Application No. PCT/US2019/033314 dated Aug. 9, 2019.
International Preliminary Report on Patentability for Application No. PCT/US2019/033314 dated Dec. 3, 2020.
Askes et al., Activation of a photodissociative ruthenium complex by triplet-triplet annihilation upconversion in liposomes. Angew Chem Int Ed Engl. Jan. 20, 2014;53(4): 1029-33. doi: 10.1002/anie. 201309389. Epub Dec. 11, 2013.
Barhoumi et al., Photothermally targeted thermosensitive polymer-masked nanoparticles. Nano Lett. Jul. 9, 2014;14(7):3697-701. doi: 10.1021/nl403733z. Epub Jun. 9, 2014.
Bechara, et al., Cell-penetrating peptides: 20 years later, where do we stand? FEBS Letters 587 (2013) 1693-1702.
Bonnet, Shifting the light activation of metallodrugs to the red and near-infrared region in anticancer phototherapy. Comments on Inorganic Chemistry. Jul. 4, 2015;35(4):179-213.
Chien et al., Near-infrared light photocontrolled targeting, bioimaging, and chemotherapy with caged upconversion nanoparticles in vitro and in vivo. ACS Nano. Oct. 22, 2013;7(10):8516-28. doi: 10.1021/nn402399m. Epub Sep. 30, 2013.

(Continued)

*Primary Examiner* — James W Rogers
(74) *Attorney, Agent, or Firm* — Wolf, Greenfield & Sacks, P.C.

(57) ABSTRACT

The present invention generally relates to particles such as nanoparticles and, in particular, to targeted nanoparticles. In some cases, the particles may have a targeting moiety that is inhibited from recognizing a target, for example, by being positioned within the particle at an internal location. The application of a stimulus, such as light, may allow the targeting moiety to interact externally of the particle. Accordingly, the particles may be targeted to specific locations using the application of a suitable stimulus. For instance, in one embodiment, particles containing cell-penetrating peptides attached via a first attachment and a second attachment containing a photocleavable entity may be administered to a subject, and light may be applied, e.g., to the eye, to cleave the photocleavable entity. However, despite the cleavage, the peptides remain associated with the particle via the first attachment, and thus, the particles may be able to penetrate cells within the eye due to peptides. Other aspects are generally directed to methods of making or using such particles, kits involving such particles, or the like.

12 Claims, 16 Drawing Sheets

Specification includes a Sequence Listing.

(56) References Cited

OTHER PUBLICATIONS

Chu et al., Topical ocular delivery to laser-induced choroidal neovascularization by dual internalizing RGD and TAT peptide-modified nanoparticles. Int J Nanomedicine. Feb. 17, 2017;12:1353-1368.
Dou et al., Bioimaging and biodetection assisted with TTA-UC materials. Drug Discov Today. Sep. 2017;22(9):1400-1411. doi: 10.1016/j.drudis.2017.04.003. Epub Apr. 19, 2017.
Dvir et al., Photo-targeted nanoparticles. Nano Lett. Jan. 2010;10(1):250-4. doi: 10.1021/nl903411s.
Fan et al., Photocontrolled targeted drug delivery: photocaged biologically active folic acid as a light-responsive tumor-targeting molecule. Angew Chem Int Ed Engl. Aug. 27, 2012;51(35):8806-10. doi: 10.1002/anie.201203339. Epub Jul. 25, 2012.
Gray et al., Triplet-triplet annihilation photon-upconversion: towards solar energy applications. Phys Chem Chem Phys. Jun. 14, 2014;16(22):10345-52.
Hansen et al., Constrained and UV-activatable cell-penetrating peptides for intracellular delivery of liposomes. J Control Release. Nov. 28, 2012;164(1):87-94. doi: 10.1016/j.jconrel.2012.10.008. Epub Oct. 17, 2012.
Johnson et al., Cell-penetrating Peptide for Enhanced Delivery of Nucleic Acids and Drugs to Ocular Tissues Including Retina and Cornea. Molecular Therapy, 16(1):107-114, 2008.
Lee et al., Light-triggered in vivo activation of adhesive peptides regulates cell adhesion, inflammation and vascularization of biomaterials. Nat Mater. Mar. 2015;14(3):352-60. doi: 10.1038/nmat4157. Epub Dec. 15, 2014.
Li et al., Aptamer photoregulation in vivo. Proc Natl Acad Sci U S A. Dec. 2014 ;111(48):17099-103. doi: 10.1073/pnas.1420105111. Epub Nov. 17, 2014.
Liu et al., A general strategy for biocompatible, high-effective upconversion nanocapsules based on triplet-triplet annihilation. J Am Chem Soc. Apr. 3, 2013;135(13):5029-37. doi: 10.1021/ja3104268. Epub Mar. 19, 2013.
Liu et al., Blue-emissive upconversion nanoparticles for low-power-excited bioimaging in vivo. J Am Chem Soc. Mar. 21, 2012;134(11):5390-7. doi: 10.1021/ja3003638. Epub Mar. 9, 2012.
Petersen et al., Phototriggering of cell adhesion by caged cyclic RGD peptides. Angew Chem Int Ed Engl. 2008;47(17):3192-5. doi: 10.1002/anie.200704857.
Shamay et al., Light induced drug delivery into cancer cells. Biomaterials. Feb. 2011;32(5):1377-86. doi: 10.1016/j.biomaterials. 2010.10.029. Epub Nov. 12, 2010.
Sun et al., Upconversion in Nanostructured Materials: From Optical Tuning to Biomedical Applications. Chem Asian J. Feb. 16, 2018;13(4):373-385. doi: 10.1002/asia.201701660. Epub Jan. 17, 2018.
Tian et al., In vivo biodistribution and toxicity assessment of triplet-triplet annihilation-based upconversion nanocapsules. Biomaterials. Jan. 2017;112:10-19. doi: 10.1016/j.biomaterials.2016.10.008. Epub Oct. 8, 2016.
Turshatov et al., Micellar carrier for triplet-triplet annihilation-assisted photon energy upconversion in a water environment. New Journal of Physics. Aug. 31, 2011; 13:083035.
Wang et al., Efficient Triplet-Triplet Annihilation-Based Upconversion for Nanoparticle Phototargeting. Nano Lett. Oct. 14, 2015;15(10):6332-8. doi: 10.1021/acs.nanolett.5b01325. Epub Jul. 9, 2015.
Wang et al., Intravenous treatment of choroidal neovascularization by photo-targeted nanoparticles. Nat Commun. Feb. 18, 2019;10(1):804.
Yang et al., Preparation and characterization of photo-responsive cell-penetrating peptide-mediated nanostructured lipid carrier. J Drug Target. Dec. 2014;22(10):891-900.
Yuan et al., Steric protected and illumination-activated tumor targeting accessory for endowing drug-delivery systems with tumor selectivity. Adv. Funct. Mater. 2014, 24, 1799-1807.
Zhang et al., Thiol-activated triplet-triplet annihilation upconversion: study of the different quenching effect of electron acceptor on the singlet and triplet excited states of Bodipy. J Org Chem. Jun. 5, 2015;80(11):5674-86.
Zhou et al., Upconversion luminescent materials: advances and applications. Chem Rev. Jan. 14, 2015;115(1):395-465. doi: 10.1021/cr400478f. Epub Dec. 10, 2014.
EP 16818746.6, Dec. 3, 2018, European Office Action.
EP 16818746.6, Mar. 28, 2019, Extended European Search.
PCT/US2016/040271, dated Oct. 13, 2016, International Search Report and Written Opinion.
PCT/US2016/040271, Jan. 11, 2018, International Preliminary Report on Patentability.
PCT/US2019/033314, Aug. 9, 2019, International Search Report and Written Opinion.
PCT/US2019/033314, Dec. 3, 2020, International Preliminary Report on Patentability.

* cited by examiner

SEQUENCE LISTING

```
<160> NUMBER OF SEQ ID NOS: 13

<210> SEQ ID NO 1
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 1

Cys Gly Gly Phe Arg Lys Lys Arg Arg Gln Arg Arg Arg
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 3

Gly Arg Lys Lys Arg Arg Gln Arg Arg Arg Pro Pro Gln
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 4

Leu Leu Ile Ile Leu Arg Arg Arg Ile Arg Lys Gln Ala His Ala His
1               5                   10                  15

Ser Lys

<210> SEQ ID NO 5
<211> LENGTH: 27
<212> TYPE: PRT
<213> ORGANISM: Artificial Sequence
<220> FEATURE:
<223> OTHER INFORMATION: Synthetic polypeptide
```

-continued

```
<400> SEQUENCE: 5

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 6
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 6

Gly Ala Leu Phe Leu Gly Phe Leu Gly Ala Ala Gly Ser Thr Met Gly
1               5                   10                  15

Ala Trp Ser Gln Pro Lys Lys Arg Lys Val
            20                  25

<210> SEQ ID NO 7
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 7

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 8
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(12)
<223> OTHER INFORMATION: may be absent

<400> SEQUENCE: 8

Arg Arg Arg Arg Arg Arg Arg Arg Arg Arg Arg Arg
1               5                   10

<210> SEQ ID NO 9
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 9

Lys Leu Ala Leu Lys Leu Ala Leu Lys Ala Leu Lys Ala Ala Leu Lys
1               5                   10                  15

Leu Ala

<210> SEQ ID NO 10
<211> LENGTH: 9
<212> TYPE: PRT
<213> ORGANISM: Artificial Sequence
<220> FEATURE:
<223> OTHER INFORMATION: Synthetic polypeptide
```

```
<400> SEQUENCE: 10

Arg Arg Trp Trp Arg Arg Trp Arg Arg
1               5

<210> SEQ ID NO 11
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 11

Cys Gly Gly Gly Ala Arg Lys Lys Ala Ala Lys Ala Ala Arg Lys Lys
1               5                   10                  15

Ala Ala Lys Ala Ala Arg Lys Lys Ala Ala Lys Ala Ala Arg Lys Lys
            20                  25                  30

Ala Ala Lys Ala
        35

<210> SEQ ID NO 12
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 12

Cys Gly Gly Phe Arg Lys Lys Arg Arg Gln
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 13

Cys Tyr Gly Gly Arg Gly Asn Gly
1               5
```

NANOPARTICLES FOR TREATMENT OF CHOROIDAL NEOVASCULARIZATION AND OTHER INDICATIONS

RELATED APPLICATIONS

This application is a national stage filing under 35 U.S.C. § 371 of international application number PCT/US2019/033314, filed May 21, 2019, which claims the benefit of U.S. Provisional Patent Application Ser. No. 62/675,026, filed May 22, 2018, entitled "Nanoparticles for Treatment of Choroidal Neovascularization and Other Indications," by Kohane, et al., each of which are incorporated herein by reference in their entirety.

GOVERNMENT FUNDING

This invention was made with government support under Grant Nos. GM 116920 awarded by National Institutes of Health. The government has certain rights in the invention.

FIELD

The present invention generally relates to particles such as nanoparticles and, in particular, to targeted nanoparticles.

BACKGROUND

Retinopathy of prematurity, diabetic retinopathy, and vascular age-related macular degeneration (AMD) are leading causes of blindness in infants, adults and the elderly in the U.S., respectively. These diseases of varying etiology are all characterized by the development of pathogenic neovascularization, which disrupts retinal structure and function, causing irreversible vision loss. Currently, the standard therapies for the treatment of neovascular eye diseases are laser photocoagulation and repeated intravitreal injections of antibodies against vascular endothelial growth factor. They are effective in slowing or preventing neovascularization, but suffer from serious side effects—for example, laser treatment inevitably destroys retinal tissue, and intraocular injections are unpleasant for the patients and bear risks of endophthalmitis and retinal detachment. Less invasive means of administration of therapeutics, for example by intravenous injection, is therefore desirable. However, systemic administration of drugs often results in inadequate concentrations of drugs at the diseased site; this is particularly true of delivery to the back of the eye (retina and associated structures). Increasing drug levels at the target site by increasing the dose could lead to systemic toxicity. Recent advances in nanoparticle-based drug delivery systems (DDSs) provide opportunities to improve drugs' therapeutic effects. DDSs that enable drug delivery to the back of the eye are administered locally by intravitreal injection, or systemically. Systemic DDS can reach diseased sites due to the leaky vasculature in neovascular eye diseases, or by targeting the ligand-modified DDS to specific antigens. Such targeting is impeded by variability in the expression of ligand receptor at the diseased site and, by the basal expression of certain target antigens (e.g., endoglin, integrin) in normal tissue. Accordingly, improvements in delivery are still needed.

SUMMARY

The present invention generally relates to particles such as nanoparticles and, in particular, to targeted nanoparticles. The subject matter of the present invention involves, in some cases, interrelated products, alternative solutions to a particular problem, and/or a plurality of different uses of one or more systems and/or articles.

According to one aspect, the present invention is generally directed to a composition. In some cases, the composition may be applicable to a subject, or a part thereof. For example, the composition may be applicable to the eye of a subject.

In one set of embodiments, the composition comprises a polymeric particle comprising a core and a shell, and an activatable agent present within the shell. In some cases, the activatable agent comprises a photocleavable entity and a targeting moiety comprising a targeting moiety. The targeting moiety may be inhibited from recognizing a target in certain instances.

In another set of embodiments, the composition comprises a particle comprising a core and a shell, and an activatable agent present within the shell. According to some embodiments, the activatable agent may comprise a targeting moiety and a cleavable entity. In some cases, the targeting moiety is inhibited from recognizing a target. In certain embodiments, the cleavable entity is associated with the core of the particle. In addition, in certain instances, the targeting moiety is not present on an exposed surface of the particle.

In another aspect, the present invention is generally directed to a method of administering, to a subject, a plurality of polymeric nanoparticles such that at least some of the particles enter systemic circulation within the subject, the polymeric nanoparticles comprising a core, a shell, and an activatable agent present within the shell, the activatable agent comprising a cell-penetrating peptide and a photocleavable entity, wherein the cell-penetrating peptide is inhibited from recognizing a target, and applying light to an eye of the subject, wherein the light cleaves the photocleavable entity to separate at least a portion of the photocleavable entity from the activatable agent, wherein upon separation, the cell-penetrating peptide is able to recognize a target on the surface of a cell.

The method, in another set of embodiments, comprises administering, to a subject, a plurality of particles comprising a core, a shell, and an activatable agent present within the shell, where the activatable agent comprising a targeting moiety and a cleavable entity, and cleaving the cleavable entity within the subject to expose the targeting moiety on an exposed surface of the particle.

In another set of embodiments, the method comprises providing a polymeric nanoparticle comprising a core, a shell, and an activatable agent present within the shell, the activatable agent comprising a cell-penetrating peptide and a photocleavable entity, the cell-penetrating peptide being inhibited from recognizing a target, and applying light to the photocleavable entity to cleave the photocleavable entity to separate at least a portion of the photocleavable entity from the activatable agent. In some cases, upon separation, the cell-penetrating peptide is able to recognize a target on the surface of a cell.

In yet another set of embodiments, the method comprises providing a particle comprising a core, a shell, and an activatable agent present within the shell, the activatable agent comprising a targeting moiety and a cleavable entity, the targeting moiety being inhibited from recognizing a target, and cleaving the cleavable entity to separate at least a portion of the cleavable entity from the activatable agent. In some cases, upon separation of the cleavable entity, the targeting moiety may be able to recognize a target.

Several methods are disclosed herein of administering a subject with a compound for prevention or treatment of a particular condition. It is to be understood that in each such aspect of the invention, the invention specifically includes, also, the compound for use in the treatment or prevention of that particular condition, as well as use of the compound for the manufacture of a medicament for the treatment or prevention of that particular condition.

In another aspect, the present invention encompasses methods of making one or more of the embodiments described herein, for example, particles such as targeted nanoparticles, including those described herein. In still another aspect, the present invention encompasses methods of using one or more of the embodiments described herein, for example, particles such as targeted nanoparticles, including those described herein.

Other advantages and novel features of the present invention will become apparent from the following detailed description of various non-limiting embodiments of the invention when considered in conjunction with the accompanying figures.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

BRIEF DESCRIPTION OF THE SEQUENCES

Figure 1A:
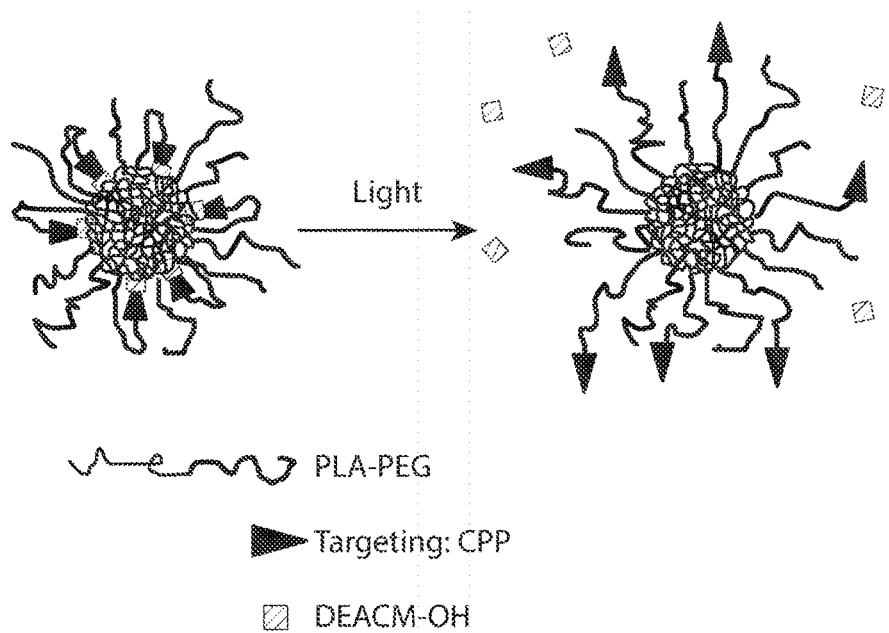
FIGS. 1A-1F illustrate certain phototargeted nanoparticles, in accordance with one set of embodiments.

SEQ ID NO: 1 is
CGGFRKKRRQRRR, a cell penetrating peptide;

SEQ ID NO: 2 is
RQIKIWFQNRRMKWKK, a cell penetrating peptide;

SEQ ID NO: 3 is
GRKKRRQRRRPPQ, a cell penetrating peptide;

SEQ ID NO: 4 is
LLIILRRRIRKQAHAHSK, a cell penetrating peptide;

SEQ ID NO: 5 is
GWTLNSAGYLLGKINLKALAALAKKIL, a cell penetrating peptide;

SEQ ID NO: 6 is
GALFLGFLGAAGSTMGAWSQPKKKRKV, a cell penetrating peptide;

SEQ ID NO: 7 is
KETWWETWWTEWSQPKKKRKV, a cell penetrating peptide;

SEQ ID NO: 8 is
$R_n$ wherein n is between 6 and 12 inclusively, a cell penetrating peptide;

SEQ ID NO: 9 is
KLALKLALKALKAALKLA, a cell penetrating peptide;

SEQ ID NO: 10 is
RRWWRRWRR, a cell penetrating peptide;

SEQ ID NO: 11 is
CGGG(ARKKAAKA)$_4$, a cell penetrating peptide;

SEQ ID NO: 12 is
CGGFRKKRRQ, a cell penetrating peptide; and

SEQ ID NO: 13 is
CYGGRGNG.

DETAILED DESCRIPTION

The present invention generally relates to particles such as nanoparticles and, in particular, to targeted nanoparticles. In some cases, the particles may have a targeting moiety that is inhibited from recognizing a target, for example, by being positioned within the particle at an internal location. The application of a stimulus, such as light, may allow the targeting moiety to interact externally of the particle. Accordingly, the particles may be targeted to specific locations using the application of a suitable stimulus. For instance, in one embodiment, particles containing cell-penetrating peptides attached via a first attachment and a second attachment containing a photocleavable entity may be administered to a subject, and light may be applied, e.g., to the eye, to cleave the photocleavable entity. However, despite the cleavage, the peptides remain associated with the particle via the first attachment, and thus, the particles may be able to penetrate cells within the eye due to peptides. Other aspects are generally directed to methods of making or using such particles, kits involving such particles, or the like.

In one aspect, the present invention is generally directed to systems and methods useful for the targeted delivery of particles into specific locations within the body. For example, in one embodiment, particles may be administered to a subject, and the particles may then enter systemic circulation. The particles do not contain any surface features, such as targeting moieties, that allow the particles to be introduced into cells, and thus, the particles are able to remain in systemic circulation. However, the particles may subsequently be altered in some fashion, e.g., upon exposure to light or another stimulus, that causes the particles to exhibit a targeting moiety on their surfaces. The targeting moiety can then allow the particles to be delivered to cells at a specific location of the body, for example, near the region where the light or other stimulus is applied. Thus, localized delivery of the particles can be achieved by the suitable application of light (or other stimulus) to a specific location of the body, while the particles otherwise generally remain in circulation.

As a non-limiting example, particles may be administered systemically to a subject, while light of a certain wavelength applied to the eyes to cause particles within the eye to penetrate cells. Accordingly, drugs contained within the particles may specifically be delivered to an eye of a subject, even though the particles are systemically applied.

A variety of techniques may be used to create particles where the surface features are controllable, e.g., upon application of light or another stimulus. As a non-limiting example, a particle may contain a cell-penetrating peptide as a targeting moiety, attached to the particle via a first attachment and a second attachment. A specific example is illustrated in FIG. 1A, left. The cell-penetrating peptides may be positioned within the particle via the attachments such that they are inhibited from functioning. For instance, the peptides may be positioned internally of the particle (e.g., such that they are not exposed to the surface), and/or there may be a blocking group positioned to prevent the peptides from being able to recognize a cell, for example, due to steric effects, distortion of the peptide, physical blockage, or the like.

In some cases, the second attachment may be cleavable in some fashion. For instance, the second attachment may include a photocleavable moiety, such as 7-(diethylamino) coumarin-4-yl]methyl carboxyl (DEACM), that may be cleaved upon exposure to light, e.g., of a suitable wavelength, e.g., as is shown in FIG. 1A, right. When that light is applied, the photocleavable moiety may be cleaved, thereby detaching the cell-penetrating peptide at its second point of attachment. However, the peptide is not then free to drift away from the particle, as it is still attached at a first point of attachment. Attachment at the first point of attachment may allow the peptide to be exposed at the surface of the particle, e.g., as the peptide may still be "tethered" to the particle (for example, as show in FIG. 1A), or because the blocking group no longer blocks access to the peptide. In such a fashion, the cell-penetrating peptide can then recognize cells, and may accordingly facilitate delivery of the particles into those cells.

The above discussion is a non-limiting example of one embodiment of the present invention that is generally directed to particles, such as nanoparticles, that can be used for targeted delivery to the eye of a subject. However, other embodiments are also possible. Accordingly, more generally, various aspects of the invention are directed to various systems and methods generally directed to particles such as nanoparticles.

Some aspects of the present invention are generally directed to particles, such as nanoparticles, having a core region and a shell region. The core and the shell may have different hydrophobicities, e.g., the core may be relatively hydrophobic and the shell may be relatively hydrophilic, relative to each other. For example, the core may be formed from one or more polymers having a water contact angle of at least 90°, while the shell may be formed from one or more polymers having a water contact angle of less than 90°. Examples of such polymers, and dimensions of such particles, are described in more detail below.

The particle may include an activatable agent that can be controlled to allow access to a targeting entity. For example, prior to activation, the targeting entity may be inhibited from recognizing a target, but after activation, at least some of the targeting entity can then recognize a target. As examples, the targeting entity may be positioned within the particle, e.g., such that the targeting moiety is present within and/or contacts the core of the particle, such that the targeting moiety is not present on an outer surface of the particle, the targeting entity may be blocked by another portion of the activation entity such that it cannot recognize a target, the targeting entity is in a molecular configuration such that it cannot recognize a target, or the like. Thus, for example, the targeting entity may be distributed within the particle such that at least 50%, at least 60%, at least 70%, at least 80%, at least 90%, at least 95%, or substantially all of the targeting entity (by mass) is not present on the surface of the particle, and/or is present but cannot recognize a target, e.g., due to conformation, blockage, or the like.

In one set of embodiments, the activatable agent may include a cleavable entity and a targeting moiety. As discussed below, the targeting moiety may be able to recognize a target, while the cleavable entity may be cleaved to activate the activatable agent to allow the targeting moiety may be able to recognize a target.

In some cases, the activatable agent may be attached to a polymer forming the particle. For instance, as is shown in FIG. 10, an activatable agent 10 may comprise a first portion comprising a targeting moiety 11 and a second portion comprising a cleavable entity 12. The targeting moiety and the cleavable entity may be present within the activatable agent in any suitable order, in addition to the order shown here. The first portion may be attached to a polymer 13, while the second portion may be relatively hydrophobic and may thus associate with a hydrophobic region of a particle 20, e.g., a core region 21, while polymer 13 may be present within a shell region 22. Due to the association of the second portion with the hydrophobic region, the first portion of the activatable agent containing the targeting moiety may not be present on the outer surface of the particle, or may be present on the outer surface but be inhibited from being able to recognize a target, e.g., due to the conformation of the activatable agent. However, cleavage of the cleavable entity may then separate the first portion and the second portion of the activatable agent, which may allow the first portion, containing the targeting moiety, to reach the outer surface of the particle, or otherwise allow it to recognize an appropriate target.

The targeting entity may be any entity able to recognize an appropriate target. A variety of moieties may be used as the targeting moiety. In one set of embodiments, the targeting moiety may comprise a peptide, e.g., one that can recognize a suitable target. For example, the targeting moiety may comprise an RGD peptide (e.g., which can bind to for example, which can bind to certain extracellular matrix proteins, such as fibronectin), or a cell-penetrating peptide (CPP).

A wide variety of cell-penetrating peptides are known. For example, the cell-penetrating peptide may be a Tat-C cell-penetrating peptide, a Tat(48-60) cell-penetrating peptide, or a Tat(48-57) cell-penetrating peptide. Other non-limiting examples of cell-penetrating peptides include CGG-FRKKRRQRRR (SEQ ID NO: 1), RQIKIWFQNRRMKWKK (SEQ ID NO: 2), GRKKRRQRRRPPQ (SEQ ID NO: 3), LLIILRRRIRKQA-HAHSK (SEQ ID NO: 4), GWTLNSAGYLLGKINLKA-LAALAKKIL (SEQ ID NO: 5), GALFLGFL-GAAGSTMGAWSQPKKKRKV (SEQ ID NO: 6), KETWWETWWTEWSQPKKKRKV (SEQ ID NO: 7), $R_n$ wherein n is between 6 and 12 inclusively (i.e., 6, 7, 8, 9, 10, 11, or 12) (SEQ ID NO: 8), KLALKLALKALKAALKLA (SEQ ID NO: 9), RRWWRRWRR (SEQ ID NO: 10), CGGG(ARKKAAKA)$_4$ (SEQ ID NO: 11), or CGG-FRKKRRQ (SEQ ID NO: 12)

In some cases the peptide may have less than 50, less than 40, less than 30, less than 25, less than 20, or less than 15 amino acid residues. In certain cases, the peptide may have at least 5, at least 10, or at least 15 amino acid residues.

Other targeting moieties are also possible. For example, the targeting moiety may comprise an antibody, an antibody fragment, an antigen, a binding partner for a cell-surface receptor, or the like. Specific examples include, but are not limited to, anti-CD13 antibodies, NGR peptides that recognizes CD143 (e.g., having a sequence CYGGRGNG (SEQ ID NO: 13)), transferrin, phage-derived human antibody fragments having high affinity for the ED-B domain of fibronectin (e.g., L19), anti-integrin $\alpha_v\beta_3$ (alpha-5-beta-3) monoclonal antibodies, and nucleic acid aptamers.

The cleavable entity may be any entity that can be cleaved, e.g., in response to an appropriate stimulus. For example, a photocleavable entity can be cleaved upon exposure to light of a suitable wavelength, e.g., visible light and/or ultraviolet light. In some cases, the applied light may be light having an average wavelength of between 300 nm and 500 nm, between 350 nm and 450 nm, between 400 nm and 700 nm, between 10 nm and 400 nm, between 570 nm and 900 nm, or the like. As another example, a cleavable entity may be cleaved upon exposure to heat. For instance, the heat may be generated by magnetic field, light or ultrasound. In some cases, for instance, the cleavable entity may be a nucleic acid (or a pair of nucleic acids) that is cleaved via heat-induced dehybridization of the nucleic acid.

In one set of embodiments, the photocleavable entity is coumarin-based, e.g., having a coumarin-based photocaging group. Other examples of photocleavable entities include o-nitrobenzyl, benzoinyl(desyl), 4-hydroxyphenacyl and ruthenium-based photocaging groups. As a specific non-limiting example, the photocleavable entity may be 7-(diethylamino) coumarin-4-yl]methyl carboxyl (DEACM). In some cases, the coumarin photocaging group modified at the 3-position, e.g., as is discussed in Lin, et al., "Coumarin Photocaging Groups Modified with an Electron-Rich Styryl Moiety at the 3-Position: Long-Wavelength Excitation, Rapid Photolysis, and Photobleaching," *Ang. Chem. Int. Ed.*, 57(14):3722-3726, 2018, all of the coumarin and other photocaging moieties of which are incorporated herein by reference.

In some embodiments, the cleavable entity may be relatively hydrophobic. For instance, the cleavable entity may be able to associate with the core region of a particle having a core region and a shell region, which may inhibit the targeting moiety from reaching the outer surface of the particle or allowing it to recognize an appropriate target. In certain embodiments, for example, the cleavable entity may preferentially associate with the polymers that form the core region, relative to the polymers that from the shell region. The cleavable entity may exhibit a water contact angle of at least 90° in some embodiments.

As discussed, the particle may comprise a core and a shell, and may be spherical or non-spherical. Spherical particles may be particularly useful in some embodiments, for example, to facilitate cellular uptake. The particle may have any suitable diameter. In some cases, the particle can be a nanoparticle, e.g., having an diameter measured in nanometers. For instance, the particle may have a hydrodynamic diameter of less than 1000 nm, less than 500 nm, less than 300 nm, less than 100 nm, less than 50 nm, less than 30 nm, or less than 10 nm. The diameter of the core may be, for example, less than 1000 nm, less than 500 nm, less than 300 nm, less than 100 nm, less than 50 nm, less than 30 nm, or less than 10 nm. The particles may also have an average diameter of less than about 1 mm, less than about 500 micrometers, less than about 300 micrometers, less than about 100 micrometers, less than about 50 micrometers, less than about 30 micrometers, less than about 10 micrometers, less than about 5 micrometers, less than about 3 micrometers, or less than about 1 micrometer, etc. The hydrodynamic diameter may be measured using laser light scattering, or other techniques known by those of ordinary skill in the art. The average diameter of a nonspherical particle may be taken as the volume of a perfect sphere having the same volume of the particle. The particle may also be larger than a nanoparticle in some embodiments.

In one set of embodiments, the particle is formed from a polymer. For instance, the particle may be a micelle, e.g., formed of polymers. Any suitable polymer can be used for the particle. Examples of polymers include, but are not limited to, polylactic acid, polyglycolic acid, polyethylene oxide, polystyrene, polyethylene, polypropylene, etc. In some embodiments, the polymer may be biodegradable or biocompatible, e.g., for use in various medical or biological applications. In some cases, more than one polymer can be used, e.g., to form a core-shell structure. In some cases, one or more polymers may be physically and/or chemically combined, e.g., as in a copolymer. As a non-limiting example, the particle may include a copolymer such as poly(D,L-lactic acid)-poly(ethylene oxide). However, it should be understood that the particle need not be limited to polymeric materials. For example, in other embodiments, the particle can include silica, ceramics, or other materials.

In certain embodiments, the core may be hydrophobic, while the shell may be hydrophilic. The core and the shell may each be defined by one or more polymers. For example, the core may have a first polymer and the shell may have a second polymer. The first polymer may be hydrophobic in some cases, e.g., having a water contact angle of at least 90°, while the second polymer may be hydrophilic, e.g., having a water contact angle of less than 90°. In some embodiments, the first polymer may be relatively hydrophobic while the second polymer may be relatively hydrophilic, e.g., relative to each other. In addition, in some cases, the first and second polymers may be joined to each other, e.g., as in a polymer, such as a block copolymer, a graft copolymer, or the like.

Non-limiting examples of hydrophilic polymers that can be used for the first polymer include polylactic acid (PLA), polyglycolic acid (PGA), poly(lactic-co-glycolic) acid (PLGA), poly(glycerol sebacate) (PGS), or the like. Non-limiting examples of hydrophobic polymers that can be used for the second polymer include poly(ethylene glycol) (PEG), methoxy poly(ethylene glycol) (mPEG) or certain zwitterionic polymers. In some cases, one or both of the first and the second polymers may be biocompatible, biodegradable, and/or bioresorbable. The polymers may each have any suitable molecular weight. For example, the molecular weight of the first polymer and second polymer may each independently be at least 500, at least 1,000, at least 2,000, at least 3,000, at least 4,000, or at least 5,000, and/or no more than 5,000, no more than 4,000, no more than 3,000, no more than 2,000, or no more than 1,000.

In some embodiments, the hydrophilic polymer and the hydrophobic polymer may be selected to have a ratio of molecular weights that is at least 0.2, at least 0.3, at least 0.5, at least 0.8, at least 1, at least 1.2, at least 1.5, at least 2, at least 3 or at least 5. The ratio may also be less than 5, less than 3, less than 2, less than 1.5, less than 1, less than 0.8, less than 0.5, less than 0.3, less than 0.2, etc. Combinations of any of these ratios are also possible, e.g., the ratio may be between 0.5 and 1.5, between 0.3 and 0.8, between 1 and 1.5, etc. Without wishing to be bound by any theory, it is believed that suitable ratios of polymers may facilitate cellular uptake.

A variety of methods may be used to bind or otherwise incorporate one or more of the cleavable entity and the targeting moiety within the activatable agent, which may also optionally be bound to one or more polymers within the particle.

For example, the cleavable entity and the targeting moiety may be bound directly to each other, or there may be one or more other moieties positioned between them. As an example, if the targeting moiety comprises an amine, then the cleavable entity may be directly bound to the amine, e.g., via an amide bond, click chemistry, or the like. The cleavable entity may in some cases be directly bound to carboxylic acid via an ester bond or a thioester bond. In certain cases where the targeting moiety comprise a protein, then the amine may be an amine of an amino acid residue, e.g., as in lysine, arginine, histidine, etc. The amine may be anywhere within the peptide, e.g., at a terminal end (e.g., the C-terminal end), or elsewhere within the peptide.

In some embodiments, the activatable agent may be bound to a polymer directly, or there may be one or more other moieties positioned between them. The polymer may be hydrophilic or hydrophobic, and may be a block copolymer or any other polymer described herein. As a non-limiting example, the activatable agent may be directly covalently bound to a second polymer of a block copolymer as discussed herein, e.g., via direct binding of the targeting moiety, or the like.

For example, in one set of embodiments, a thiol group within the targeting moiety may be bound to a maleimide group attached to the polymer. In certain cases where the targeting moiety comprise a protein, then the thiol may be a thiol of an amino acid reside, e.g., as in cysteine. The thiol may be anywhere within the peptide, e.g., at a terminal end (e.g., the N-terminal end), or elsewhere within the peptide.

Other examples of attaching the targeting moiety directly to the polymer include, but are not limited to, a coupling of 2 thiol groups, a coupling of 2 primary amines, a carboxylic acid and primary amine coupling, a hydrazide and an aldehyde coupling, or a primary amine and aldehyde coupling.

The activatable agent may be present at any suitable concentration within the particle. For example, the activatable agent may be present at a concentration of at least 10%, at least 20%, at least 30%, at least 40%, at least 50%, at least 60%, at least 70%, at least 80% by mass within the particle, and/or at a concentration of no more than 80%, no more than 70%, no more than 60%, no more than 50%, no more than 40%, no more than 30%, no more than 20% by mass within the particle. Combinations of these are also possible, e.g., the activatable agent may be present at a concentration of between 20% and 60%, between 30% and 60%, between 40% and 50%, between 20% and 40%, etc. Similarly, the targeting moiety and/or the cleavable entity may be present at any suitable concentration within the particle, including any of the percentages described within this paragraph. For instance, the targeting moiety may be present at a concentration of at least 30%, at least 40%, no more than 60%, between 30% and 60%, etc.

It should be understood that while the activatable agent may be bound to a polymer in some embodiments, this does not necessarily imply that all of the polymer must therefore be bound to an activatable agent. For instance, in some cases, less than 80%, less than 60%, less than 40%, or less than 20% by mass of the polymer may be covalently bound to an activatable agent. In addition, in some cases, at least 20%, at least 40%, at least 60%, or at least 80% of the polymer may be covalently bound to an activatable agent. Combinations of these are also possible, e.g., between about 20% and 40%, between about 20% and 60%, etc. by mass of the polymer within the particle may be bound to an activatable agent, at least in certain embodiments.

In certain embodiments, one or more drugs (or other pharmaceutical agents) may be present within the particle. These may be present at any suitable location within the particle, e.g., within the core and/or within the shell, for example, based on their hydrophobicity. For example, a hydrophobic drug may be found within the core if the core is substantially hydrophobic, while a hydrophilic drug may be found within the shell if the shell is substantially hydrophilic. In some cases, a drug may be present at the interface between the core and the shell.

In some cases, the drug is a drug for treatment of the eye. Non-limiting examples include anti-VEGF aptamer Macugen, anti-VEGF antibodies bevacizumab and ranibizumab, TNP-470 (an antibiotic with antineoplastic activity), dexamethasone (a corticosteroid), or the like.

The drug may also be for the treatment of cancer. Non-limiting examples include doxorubicin, nintedanib (a tyrosine-kinase inhibitor), mitomycin C (a chemotherapeutic), melphalan, or the like.

Still other examples of drugs include, but are not limited to, cyclophosphamides, such as Clafen, Cytoxan, or Neosar. In another example, the drug is CEV (carboplatin/etoposide phosphate/vincristine sulfate).

Accordingly, in one aspect, particles such as those described herein may be used to treat a subject. The subject may be human or non-human, for example, as described herein. In one set of embodiments, the composition may be applied to a subject for treatment to the eye. The subject may, for example, have various eye conditions in need of treatment, such as macular degeneration (e.g., age-related macular degeneration) or retinoblastoma. The composition can be applied directly to the eye, and/or applied systemically to the body such that at least some of the composition is able to travel to the eye (e.g., via the blood) such that light can be applied to the eye (or a portion of the eye) to interact with the composition as discussed herein. One or both eyes may be treated, depending on the condition of the subject. In addition, in certain instances, the subject is one that exhibits or is at risk for an eye disease, such as macular degeneration (e.g., age-related macular degeneration), retinopathy of prematurity (ROP), retinoblastoma, diabetic retinopathy, uveitis, central retinal venous occlusion, peripheral retinal occlusion, or Coats' disease. In some cases, the subject is in need of treatment of choroidal neovascularization.

In some cases, the particles may be administered such that at least some of the particles enter systemic circulation within the subject. For example, the particles may be administered through direct injection to the subject (e.g., intravenous, intra-arterial, or intramuscular delivery, or through other injection or other delivery techniques known to those of ordinary skill in the art, such as oral delivery). Additional examples of administration are discussed in more detail below. The particles may be targeted by cleaving a cleavable entity to allow the targeting entity to recognize a target at a certain site within the body, e.g., in an eye, in a tumor (e.g., during a surgical procedure), or the like, thereby allowing targeting of the particle to that site and the delivery of the drug contained within the particles.

For instance, in one set of embodiments, photocleavage of a cleavable entity may be accomplished by applying light of a certain wavelength and/or intensity to a specific location within the subject, e.g., an eye, a tumor, a cavity, or the like. In some cases, the light may be administered directly (e.g., using a laser), or the light may be guided to a suitable location, e.g., using a fiber-optic cable or the like. If applied to the eye, the light may be applied to the entire eye, or targeted at a specific location or region to the eye, e.g., the lens, cornea, iris, retina, scelra, or the like. In addition, in some cases, the light may be applied to a tumor within the eye, or to certain blood vessels within the eye, e.g., blood vessels within the retina or within a tumor, etc.

The light that is applied may be any suitable light able to cause photocleavage. For example, the light may include visible light or ultraviolet light. In some cases, the light may have an average wavelength of between 300 nm and 500 nm, or between 400 nm and 700 nm.

In one set of embodiments, the light is applied at an irradiance of at least about 1 $mW/cm^2$, at least about 2 $mW/cm^2$, at least about 5 $mW/cm^2$, at least about 10 $mW/cm^2$, at least about 20 $mW/cm^2$, at least 25 $mW/cm^2$, at least about 30 $mW/cm^2$, at least about 40 $mW/cm^2$, at least about 50 $mW/cm^2$, at least about 60 $mW/cm^2$, at least about 70 $mW/cm^2$, at least about 80 $mW/cm^2$, at least about 90 $mW/cm^2$, at least about 100 $mW/cm^2$, at least about 110 $mW/cm^2$, at least about 125 $mW/cm^2$, at least about 150 $mW/cm^2$, at least about 200 $mW/cm^2$, at least about 250 $mW/cm^2$, at least about 300 $mW/cm^2$, at least about 400 $mW/cm^2$, at least about 500 $mW/cm^2$, etc. In some cases, the light is applied at an irradiance of no more than about 1000 $mW/cm^2$, no more than about 500 $mW/cm^2$, no more than about 400 $mW/cm^2$, no more than about 300 $mW/cm^2$, no more than about 250 $mW/cm^2$, no more than about 200 $mW/cm^2$, no more than about 150 $mW/cm^2$, no more than about 125 $mW/cm^2$, no more than about 110 $mW/cm^2$, no more than about 100 $mW/cm^2$, no more than about 90 $mW/cm^2$, no more than about 80 $mW/cm^2$, no more than about 70 $mW/cm^2$, no more than about 60 $mW/cm^2$, no more than about 50 $mW/cm^2$, no more than about 40 $mW/cm^2$, no more than about 30 $mW/cm^2$, no more than about 25 $mW/cm^2$, no more than about 20 $mW/cm^2$, no more than about 10 $mW/cm^2$, no more than about 5 $mW/cm^2$, no more than about 2 $mW/cm^2$, etc. Combinations of any of the above are also possible in certain embodiments. For instance, the light may be applied at an irradiance of between about 10 $mW/cm^2$ and about 100 $mW/cm^2$.

The light may also be applied for any duration. In some cases, the duration may be 30 min or less, 20 min or less, 15 min or less, 10 min or less, 5 min or less, 3 min or less, or 1 min or less. In some cases, shorter light exposure is desirable, e.g., to reduce or minimize light-induced damage. However, it should be understood that some exposure may be necessary, e.g., to cause photocleavage. For example, light may be applied for at least 30 seconds, at least 1 min, at least 2 min, at least 3 min, at least 5 min, at least 10 min, etc. In addition, in some cases, higher light intensities may allow for shorter time exposures, or vice versa.

The light may be monochromatic light (e.g., laser or coherent light), or the light may be non-monochromatic or non-coherent in some embodiments. The light may have any suitable frequency, e.g., including the frequencies discussed herein. In some cases, the light has a frequency such that the average energy of the incident light is sufficient to cause cleavage of a photocleavable moiety.

Without wishing to be bound by any theory, it is believed that in certain embodiments, light applied to the eye may be particularly effective in targeting particles within abnormally-growing blood vessels within the eye. In some cases, it is believed that abnormally-growing blood vessels within the eye (for example, within a tumor) may exhibit pathological vasculature, i.e., such blood vessels may not be as "streamlined" as normal blood vessels, which may cause the blood flowing through those blood vessels to flow more slowly, or have a longer residence time. Because of the longer time the blood remains within those locations, particles contained within the blood in those regions can be exposed to light for a longer duration than within blood flowing through other portions of the eye. Accordingly, particles in those regions may be preferentially activated relative to particles within other locations. Thus, preferential targeting of those particles may be achieved.

As mentioned, compositions such as those discussed herein may be used in a wide variety of applications, including biological and medical applications, as well as non-biological or non-medical applications. As a non-limiting example, in one set of embodiments, a composition as discussed herein may be applied to a subject. The subject may be human or non-human. For example, the subject may be a rat, mouse, rabbit, goat, cat, dog, or the like. The composition can also be applied to any suitable sample, e.g., a biological sample, a physical sample, a chemical sample, or the like.

Other portions of a subject may also be treated in various embodiments. For instance, the composition may be applied directly to a specific location within the subject, or applied systemically to the subject such that at least some of the composition is able to travel to a location where light is to be applied. For instance, the composition may be applied to the skin (or to the blood) and light applied to a portion of the skin, e.g., to cause photocleavage or targeting of the particles to occur.

In another set of embodiments, the composition is applied to a subject to treat a tumor. The composition may be applied directly to the tumor, and/or applied systemically to the body of the subject such that at least some of the composition is able to travel to the tumor (e.g., via the blood) such that light can be applied to the tumor (or portion thereof), e.g., to cause photocleavage or targeting of the particles to occur to treat the tumor. The composition can include, for example, an anti-angiogenesis drug, an anti-inflammatory drug, a radioactive species, an anticancer drug and/or a chemotherapy drug, and light may be applied to the tumor to cause release. Such application may be targeted, e.g., by applying light directly to the tumor (or at least a portion thereof); thus, release elsewhere within the subject may be minimized by not applying light to other places. In such a fashion, release of a drug or targeting the particles, e.g., into cells may be controlled or localized at or near the tumor by applying light directly to the tumor (or portion thereof), or at least proximate the tumor. In some cases, more than one composition may be present.

In various aspects, the compositions described herein can be administered by any suitable method, e.g., contained in a solution or suspension, such as inhalation solutions, local instillations, eye drops, intranasal introductions, an ointment for epicutaneous applications, intravenous solutions, injection solutions (e.g., subcutaneous, or intravenous), or suppositories. In one set of embodiments, the composition is introduced parenterally or topically. For instance, the composition may be contained within a cream, gel, or ointment applied to the skin. In some embodiments, the composition can be applied one or more times a day, by one or more administrations per day, by fewer than one time per day, or by continuous administration, etc., until a desired therapeutic effect is achieved.

In some embodiments, the composition is introduced to the subject at a dose from, e.g., 0.01 to 100.0 mg of the composition per kg of body weight of the subject. In some cases, the dose may be at least about 0.01 mg/kg, at least about 0.03 mg/kg, at least about 0.05 mg/kg, at least about 0.1 mg/kg, at least about 0.3 mg/kg, at least about 0.5 mg/kg, at least about 1 mg/kg, at least about 3 mg/kg, at least about 5 mg/kg, at least about 10 mg/kg, at least about 30 mg/kg, at least about 50 mg/kg, and/or no more than about 100 mg/kg, no more than about 50 mg/kg, no more than about 30 mg/kg, no more than about 10 mg/kg, no more than about 5 mg/kg, no more than about 3 mg/kg, no more than about 1 mg/kg, no more than about 0.5 mg/kg, no more than about 0.3 mg/kg, no more than about 0.1 mg/kg, no more than about 0.05 mg/kg, no more than about 0.03 mg/kg, etc. Where the composition is administered as a solution, the solution may have, for example, a concentration of between about 1% to about 10% of the composition. In one set of embodiments, the composition may be, or include, a pharmaceutically acceptable derivative, e.g., for parenteral use is in a pharmaceutically acceptable solvent such as, for example, an aqueous solution including water, glucose solution, isotonic solutions of sodium chloride, buffered salt solutions, or the like. Other physiological solvents or carriers can be used in other embodiments.

As mentioned, certain aspects of the present invention provide methods of administering any composition of the present invention to a subject. When administered, the compositions of the invention are applied in a therapeutically effective, pharmaceutically acceptable amount as a pharmaceutically acceptable formulation. As used herein, the term "pharmaceutically acceptable" is given its ordinary meaning. Pharmaceutically acceptable compositions are generally compatible with other materials of the formulation and are not generally deleterious to the subject. Any of the compositions of the present invention may be administered to the subject in a therapeutically effective dose. A "therapeutically effective" amount as used herein means that amount necessary to delay the onset of, inhibit the progression of, halt altogether the onset or progression of, diagnose a particular condition being treated, or otherwise achieve a medically desirable result. When administered to a subject, effective amounts will depend on the particular condition being treated and the desired outcome. A therapeutically effective dose may be determined by those of ordinary skill in the art, for instance, employing factors such as those further described below and using no more than routine experimentation.

Any medically acceptable method may be used to administer the composition to the subject. The administration may be localized (i.e., to a particular region, physiological system, tissue, organ, or cell type) or systemic, depending on the condition to be treated. For example, the composition may be administered orally, vaginally, rectally, buccally, pulmonary, topically, nasally, transdermally, through parenteral injection or implantation, via surgical administration, or any other method of administration. Examples of parenteral modalities that can be used with the invention include intravenous, intradermal, subcutaneous, intracavity, intramuscular, intraperitoneal, epidural, or intrathecal. Examples of implantation modalities include any implantable or injectable drug delivery system. Use of an implant may be particularly suitable in some embodiments of the invention.

The implant containing the composition may be constructed and arranged to remain within the body for at least 30 or 45 days, and preferably at least 60 or 90 days, or even longer in some cases. Long-term release implants are well known to those of ordinary skill in the art.

In certain embodiments of the invention, a composition can be combined with a suitable pharmaceutically acceptable carrier, for example, as incorporated into a liposome, incorporated into a polymer release system, or suspended in a liquid, e.g., in a dissolved form, or a colloidal form, or a micellular form. In general, pharmaceutically acceptable carriers suitable for use in the invention are well-known to those of ordinary skill in the art. A pharmaceutically acceptable carrier may include non-toxic material that does not significantly interfere with the effectiveness of the biological activity of the active compound(s) to be administered, but is used as a formulation ingredient, for example, to stabilize or protect the active compound(s) within the composition before use. The carrier may be organic or inorganic, and may be natural or synthetic, with which one or more active compounds of the invention are combined to facilitate the application of the composition. The carrier may be either soluble or insoluble, depending on the application. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble. Those skilled in the art will know of other suitable carriers, or will be able to ascertain such, using only routine experimentation.

In some embodiments, the compositions of the invention include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers that may be used with the active compound. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. The compositions of the invention may be formulated into preparations in solid, semi-solid, liquid or gaseous forms such as tablets, capsules, elixirs, powders, granules, ointments, creams, gels, pastes, solutions, depositories, inhalants, injectables, or the like. Those of ordinary skill in the art will know of other suitable formulation ingredients, or will be able to ascertain such, using only routine experimentation.

In another aspect, the present invention is directed to a kit including one or more of the compositions discussed herein.

A "kit," as used herein, typically defines a package or an assembly including one or more of the compositions of the invention, and/or other compositions associated with the invention, for example, as described herein. Each of the compositions of the kit may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, and the like, for example, for using, administering, modifying, assembling, storing, packaging, preparing, mixing, diluting, and/or preserving the compositions components for a particular use, for example, to a sample and/or a subject.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the composition and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

International Patent Application No. PCT/US2016/040271, filed date, entitled "Triplet-Triplet Annihilation-Based Upconversion," by Kohane, et al., published as WO 2017/004310, is hereby incorporated herein by reference in its entirety. In addition, U.S. Provisional Patent Application Ser. No. 62/675,026, filed May 22, 2018, entitled "Nanoparticles for Treatment of Choroidal Neovascularization and Other Indications," by Kohane, et al., is also incorporated herein by reference in its entirety.

The following examples are intended to illustrate certain embodiments of the present invention, but do not exemplify the full scope of the invention.

Example 1

Choroidal neovascularization (CNV) is the major cause of vision loss in wet age-related macular degeneration (AMD). Current therapies require repeated intravitreal injections, which are painful and can cause infection, bleeding, and retinal detachment. These examples describe a drug delivery system that can be administered intravenously and accumulate in the back of the eye by light-triggered targeting. Photo-targeted nanoparticles (NP-[CPP]) were formed from PEG-PLA chains modified with a cell penetrating peptide (CPP). Cell uptake of NP-[CPP] was inactivated by attaching a photocleavable group DEACM to the CPP, which also placed [CPP] in the core of the nanoparticle, preventing it from interacting with cells. Irradiation with 400 nm (blue) light cleaved DEACM, releasing CPP from the NP core and rendering it active.

This system was evaluated in mice with laser-induced CNV. After intravenous injection of NP-[CPP], irradiation at the eye cleaved DEACM, allowing NP accumulation in the choroidal neovascular lesions. NP-[CPP] with irradiation showed greater accumulation in neovascular lesions compared to the same nanoparticles without irradiation or nanoparticles without CPP. In the same mouse CNV model, NP-[CPP] loaded with doxorubicin significantly reduced neovascular lesion size. This phototriggered targeting strategy could allow non-invasive treatment of CNV and similar diseases, and enhance the proportion of drug in diseased areas of the eye vs. other healthy parts of the eye or body.

Externally triggered targeting can enable drug delivery with high spatial and temporal resolution. Light is especially attractive as the energy source for targeting the retina, since the eye is designed to admit light. These examples illustrate a system whereby nanoparticles (NPs) are administered intravenously, and are converted to a tissue-targeting state only upon irradiation in the eye. This strategy would allow the targeted accumulation of drug to be triggered locally at the back of the eye, while minimizing drug deposition at off-target sites in healthy parts of the eye and in the rest of the body.

Photo-targeted nanoparticles were formed by self-assembly of a chemically modified poly(ethylene oxide)-poly(D,L-lactic acid) (PEG-PLA) block copolymer (FIG. 1A). The nanoparticles' surfaces were modified with Tat-C (48-57) cell penetrating peptide (CPP) as the targeting moiety due to its high cellular uptake. The biological activity of the peptide was reversibly inactivated by covalent binding to a photo-cleavable caging group, 7-(diethylamino) coumarin-4-yl] methyl carboxyl (DEACM), which was selected for its high photocleavage efficiency and relatively long (400 nm) absorption wavelength (low phototoxicity). Upon irradiation, the caging group would be removed by bond cleavage so that the peptide could readily bind to nearby cells. The DEACM-CPP functionalized nanoparticles could then enhance the accumulation of drugs at the diseased site and minimize off-target drug delivery. This approach could obviate the need for intraocular injections with their attendant risks, and improve patient compliance.

Example 2

Figure 1B:
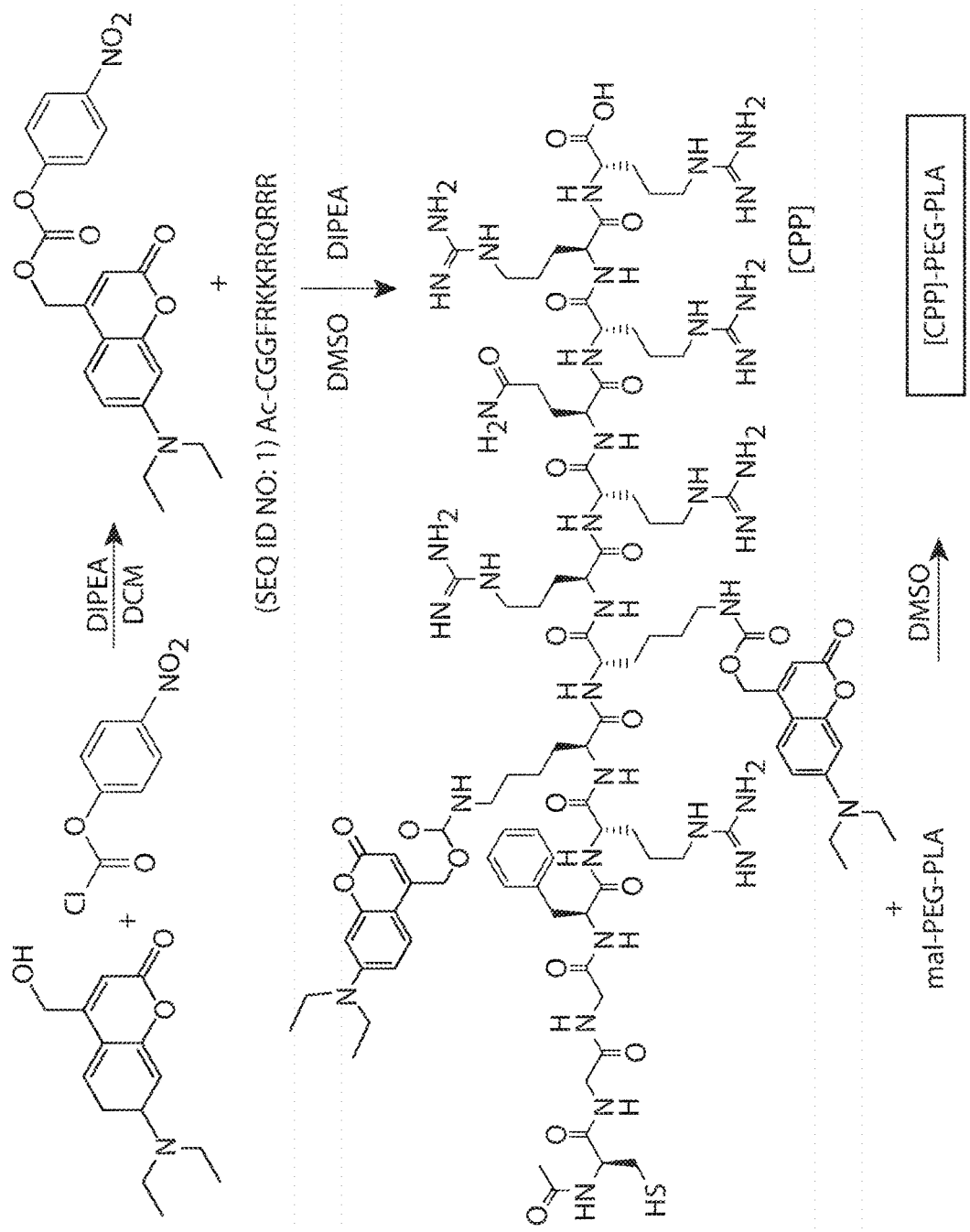
Figure 1C:
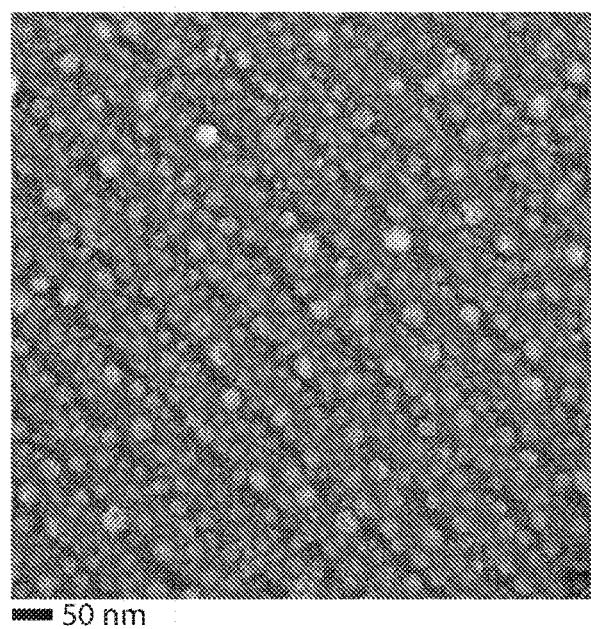

Synthesis and characterization of photo-targeted nanoparticles. FIG. 1B shows the synthesis of caged CPP ([CPP])-functionalized polymer chain, the details of which are provided below. In brief, [CPP] was synthesized by linking DEACM to the amine group on peptide side chains via nucleophilic substitution. The [CPP] with cysteine at the N-terminus (amino acid sequence acetyl-CGG-FRKKRRQRRR) (SEQ ID NO: 1) was then conjugated to the PEG end of maleimide-modified PEG-PLA via maleimide-thiol coupling. Photo-targeted nanoparticles were made by the thin-film hydration method from [CPP]-PEG-PLA and methoxy PEG-PLA (mPEG-PLA) (1:4 weight ratio). The resulting micelles, referred to as photo-targeted nanoparticles and abbreviated as NP-[CPP] (FIG. 1A), had a hydrodynamic diameter of 19.0+/−2 nm (FIG. 1C).

Figure 1D:
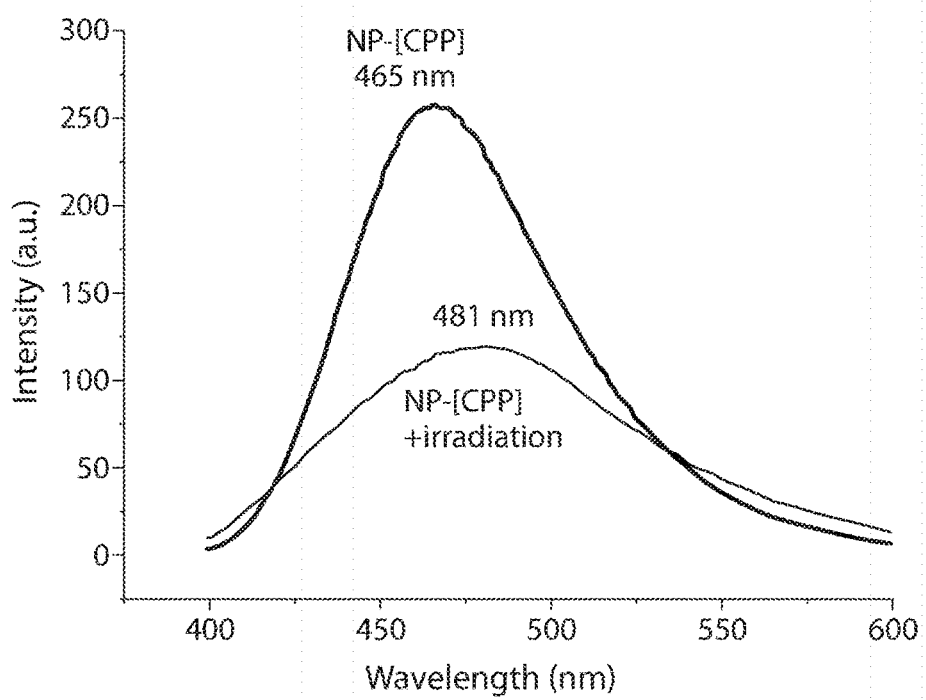
Figure 1E:
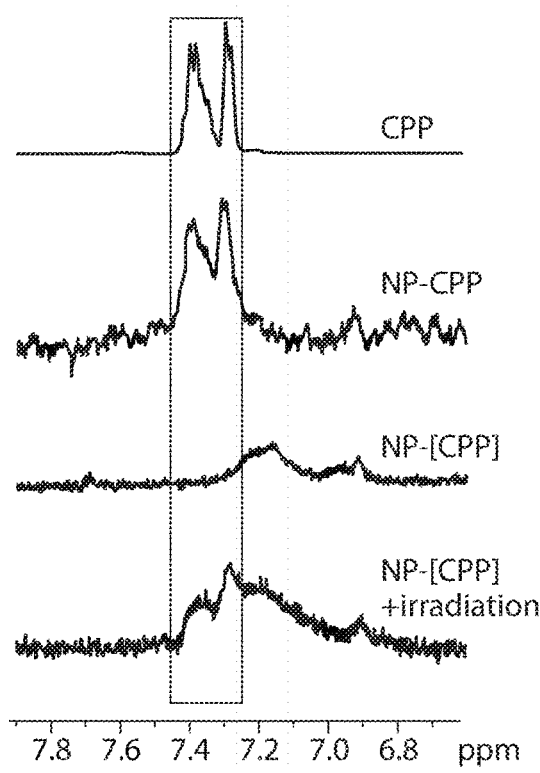

It was believed that the hydrophobic DEACM groups would localize in the PLA core of the nanoparticle, and the photocleavage reaction would release the more hydrophilic DEACM-OH into the aqueous environment. This hypothesis was supported by the fact that the fluorescence spectrum of NP-[CPP] solution showed a red shift and decrease in the emission intensity upon irradiation with 400 nm LED light (FIG. 1D). The red shift (from 465 nm to 481 nm in maximum emission wavelength) was attributable to the increased polarity of DEACM's environment and the decrease in intensity to the quenching of fluorescence by water. Further evidence indicating the presence of the CPP in the hydrophobic core was obtained by proton nuclear magnetic resonance ($^1$H NMR) spectroscopy. $^1$H NMR spectrum of NP-[CPP] did not show peaks of the phenyl protons from phenylalanine in the range of 7.25-7.45 ppm, because of the restricted mobility of the phenyl protons within the PLA cores of the nanoparticles. Irradiation resulted in the appearance of those peaks, confirming that the phenylalanine in NP-[CPP] was located in the PLA core and photocleavage led to its translocation to the surface (FIG. 1E).

Figure 1F:
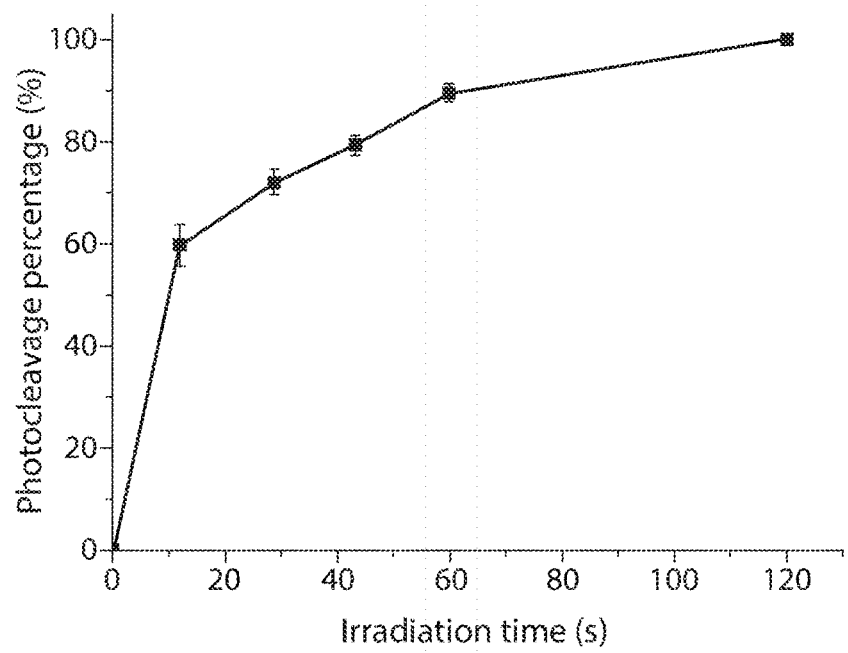

To measure the rate of phototriggered release of DEACM-OH from NP-[CPP], a quartz cuvette containing 1 mL of 0.5 mg/mL NP-[CPP] solution was continuously irradiated with 400 nm LED light at 50 mW/cm$^2$. At predetermined time points, DEACM was separated from the nanoparticle solution by centrifugation and DEACM-OH content was determined (FIG. 1f) by high-performance liquid chromatography (HPLC) ($\lambda$, lambda=390 nm). 89.7+/-1.7% of DEACM-OH was released after 1 min.

FIG. 1 shows preparation and characterization of phototargeted nanoparticles. FIG. 1A shows a schematic of light-triggered activation of the nanoparticle. FIG. 1B shows synthesis of the polymer chain functionalized with caged CPP ([CPP]). FIG. 1C is a transmission electron microscopy (TEM) image of NP-[CPP]. FIG. 1D shows fluorescence emission spectra of NP-[CPP] and NP-[CPP] irradiated for 1 min (50 mW cm$^{-2}$, 400 nm) in PBS. FIG. 1E shows $^1$H NMR spectra of free CPP and different nanoparticles in D$_2$O, with the signature phenylalanine proton peaks highlighted in the rectangle. NP-CPP is the nanoparticle formed from CPP-PEG-PLA and mPEG-PLA (1:4 weight ratio). Irradiation was with a 400 nm LED for 1 min at 50 mW cm$^{-2}$. FIG. 1F shows photocleavage of NP-[CPP] in PBS (0.5 mg mL$^{-1}$), as determined by HPLC (detected at 390 nm absorbance), after continuous irradiation (50 mW cm$^{-2}$, 400 nm) (data are means+/-SD; n=4).

Example 3

Nanoparticle uptake by cells. Cellular uptake of nanoparticles by human umbilical vein endothelial cells (HUVECs) was studied by flow cytometry and confocal microscopy in this example. Nanoparticles were labeled by addition of PEG-PLA copolymer to which the hydrophilic dye 4'-(aminomethyl) fluorescein (AMF; excitation 491 nm; emission 524 nm) was covalently bound. The weight percentage of AMF-PEG-PLA in the nanoparticles was 10%.

Figure 6A:
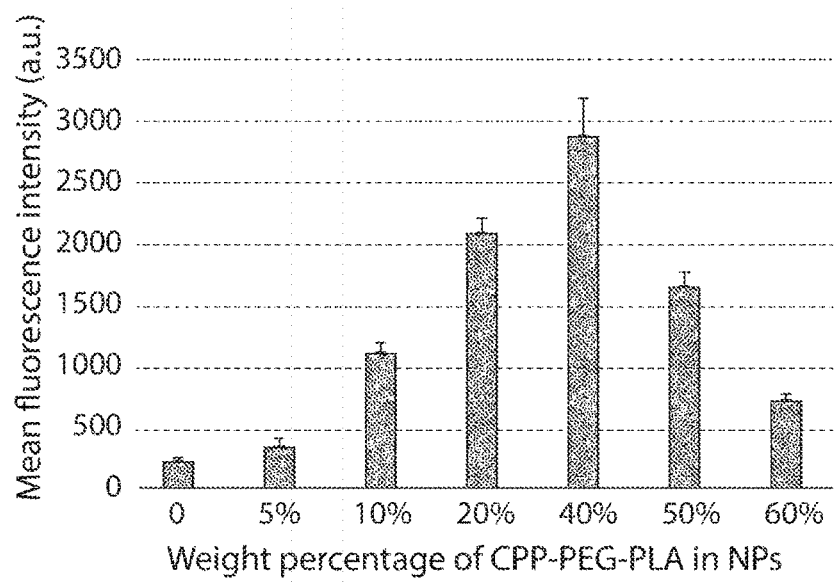
FIGS. 6A-6B illustrate uptake of particles in another set of embodiments.
Figure 6B:
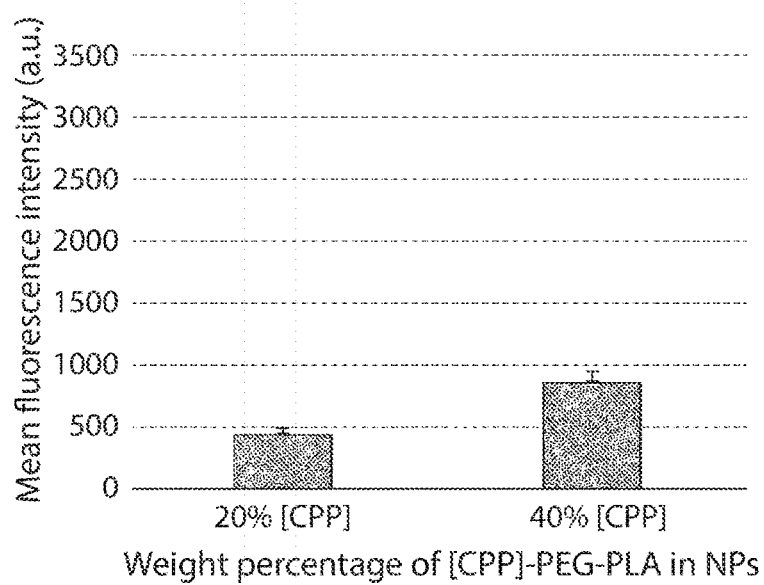

To determine the proportion of peptide-polymer conjugate to use in subsequent experiments, HUVECS were incubated with nanoparticles containing varying proportions of CPP-PEG-PLA or [CPP]-PEG-PLA. HUVEC uptake of nanoparticles increased with the proportion of CPP-PEG-PLA to a maximum at 40% w/w, then decreased at higher proportions (FIG. 6A). The effect of caging on cell uptake at the two loadings with the greatest uptake when uncaged was studied. Nanoparticles with 40% w/w [CPP]-PEG-PLA were taken up by cells to a greater extent than were nanoparticles with 20% w/w [CPP]-PEG-PLA (FIG. 6B). Given that off-target delivery remains a dominant problem even with targeted systems (also see biodistribution data below), nanoparticles with 20% w/w [CPP]-PEG-PLA were used in subsequent experiments.

FIG. 6 shows quantification of flow cytometric analyses of HUVEC uptake of nanoparticles containing different percentages of peptide-polymer conjugate. FIG. 6A shows the effect of percentage of CPP-PEG-PLA in nanoparticles on cell uptake (mean fluorescent intensity of cells). FIG. 6B shows the effect of percentage of [CPP]-PEG-PLA in nanoparticles on cell uptake. Data are means+/-SD (n=4).

HUVECs were incubated for 30 min with the following nanoparticles containing AMF-PEG-PLA: unmodified mPEG-PLA nanoparticles (NP-AMF), nanoparticles modified with CPPs (NP-AMF-CPP), NP-AMF-[CPP] without irradiation, and NP-AMF-[CPP] irradiated with a 400 nm LED (50 mW/cm$^2$, 1 min). Cell-associated AMF fluorescence was measured by flow cytometry. HUVECs incubated with NP-AMF-CPPs exhibited 9.9-fold greater fluorescence than those exposed to peptide-free nanoparticles (FIGS. 2A and 2B), which demonstrated the ability of CPP to bind nanoparticles to cells. NP-AMF-[CPP] exhibited little cell-associated fluorescence, suggesting that the caging strategy prevented ligand-mediated NP-cell interaction. Irradiation with a 400 nm LED (50 mW/cm$^2$, 1 min) increased cellular uptake to levels comparable to those with NP-AMF-CPP. These results confirmed that the DEACM caging group could be cleaved from NP-AMF-[CPP] by irradiation, which revealed CPP on the nanoparticle surface and enabled cellular uptake.

Light-controlled micelle uptake was further confirmed by confocal laser scanning microscopy. Irradiation with a 400 nm LED (50 mW/cm$^2$, 1 min) induced cell uptake of NP-AMF-[CPP] by HUVECs, whereas the uptake of non-irradiated NP-AMF-[CPP] was negligible (FIG. 2C).

Figure 2A:
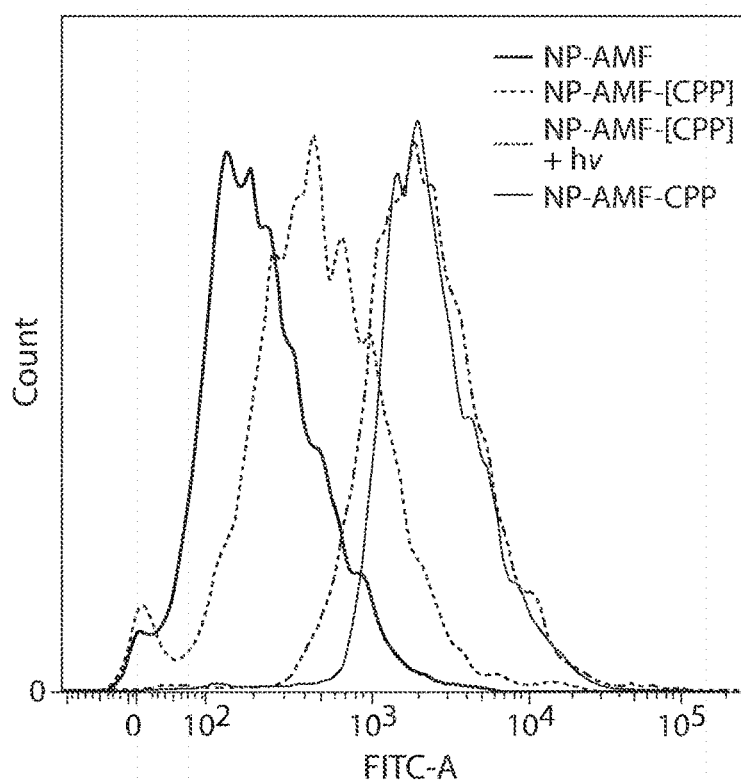
FIGS. 2A-2C illustrate light-triggered uptake, in another set of embodiments.
Figure 2B:
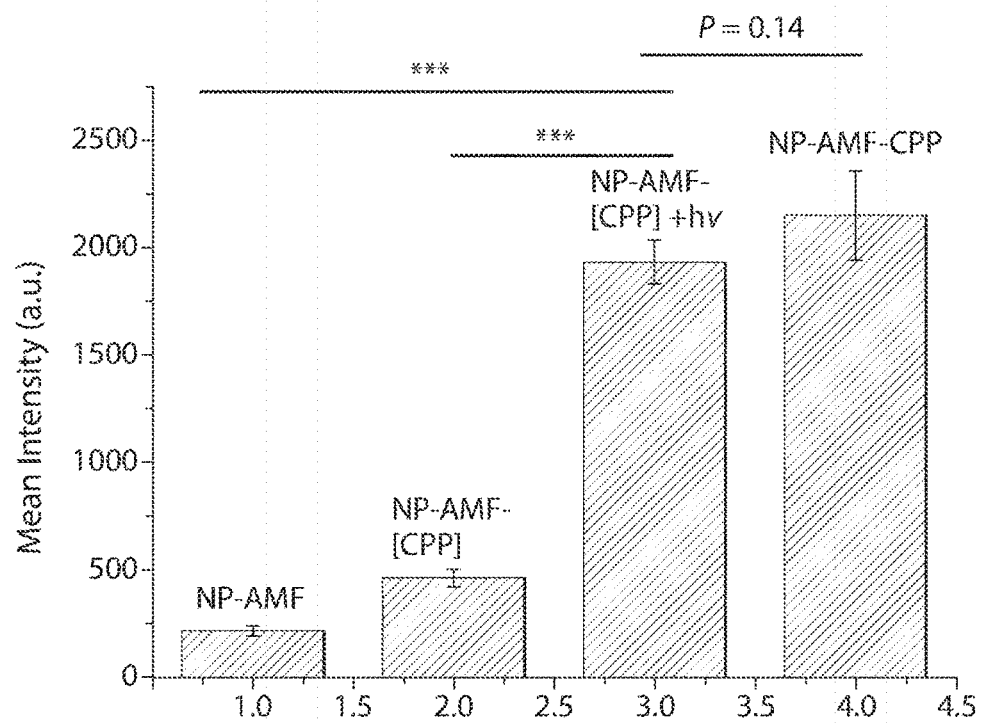
Figure 2C:
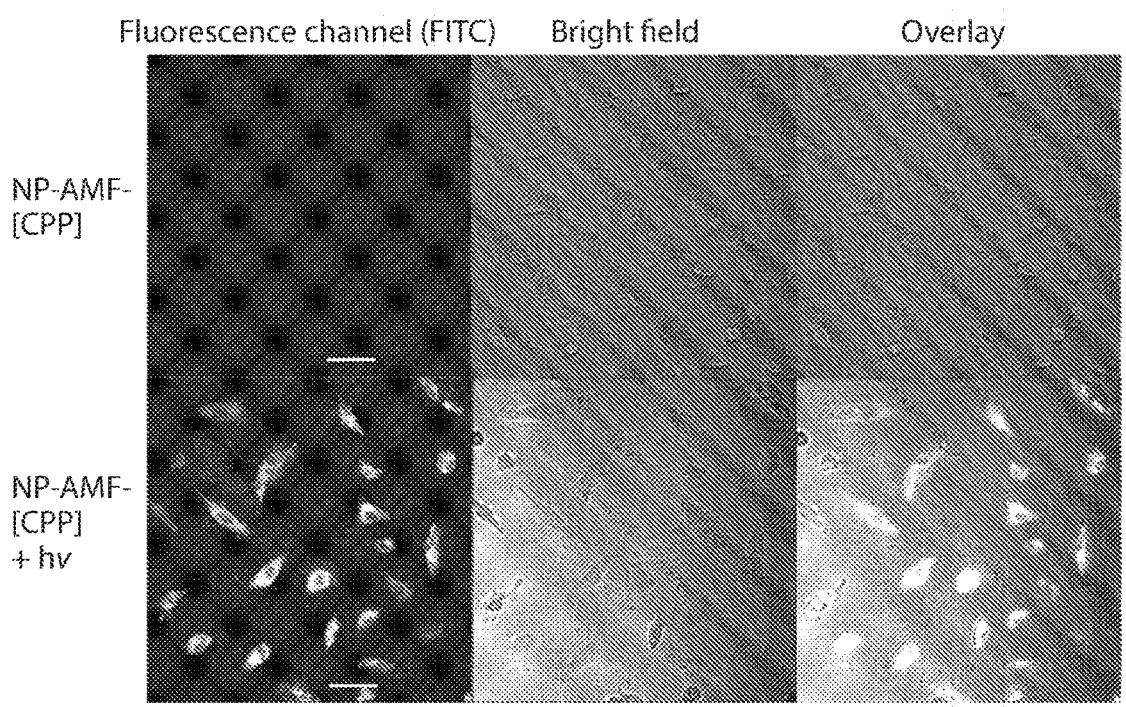
Figure 3A:
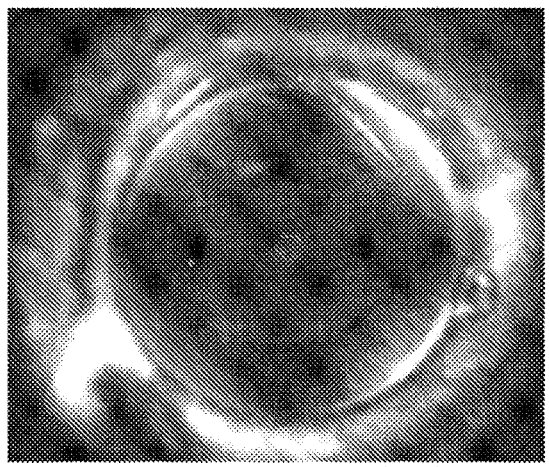
FIGS. 3A-3D illustrate light irradiation of tissue, in yet another set of embodiments.
Figure 3B:
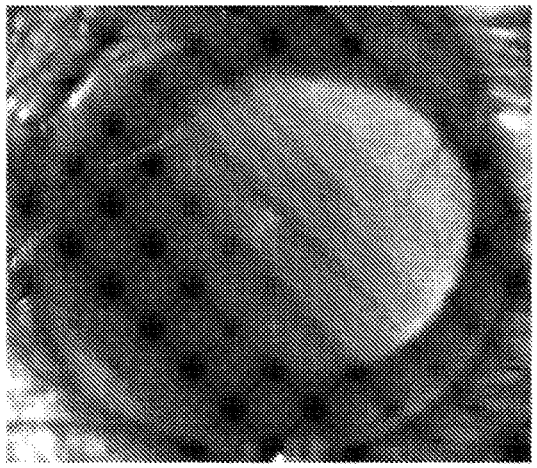
Figure 3C:
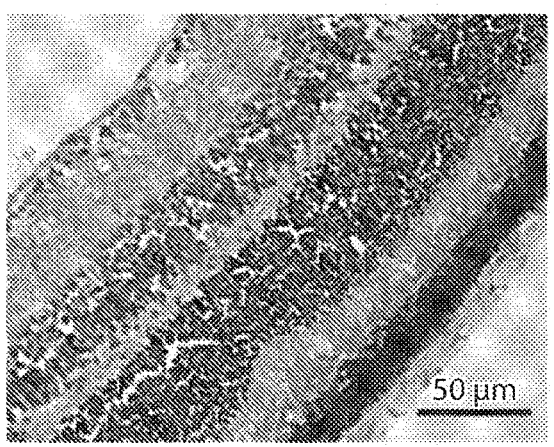
Figure 3D:
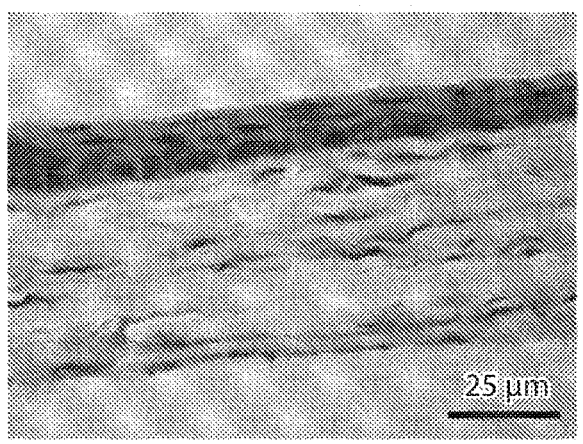

FIG. 2 shows light-triggered cell uptake of nanoparticles. FIG. 2A shows representative flow cytometry of FITC fluorescence within HUVEC cells treated with different nanoparticles. FIG. 2B shows quantitation of four flow cytometric analyses (such as the one in part A) of HUVEC uptake of nanoparticles. Data are means+/-SD (n=4). ***P<0.001. FIG. 2C shows representative confocal microscopic images of HUVEC uptake of nanoparticles. The scale bar is 20 micrometers.

Example 4

Cytotoxicity and biocompatibility of treatments. The cellular target of treatment in neovascularization is the endothelium lining the neovessels. The cytotoxicity of nanoparticles and/or irradiation in HUVECs was tested in this example. HUVECs were exposed to irradiation (400 nm LED for 1 min at 50 mW/cm$^2$), or incubated with 0.5 mg/mL NP-[CPP] overnight with irradiation (1 min, at the beginning of incubation) or without, and cell viability was assessed by the MTS assay. All three groups showed high cell viability (FIG. 7).

Figure 7:
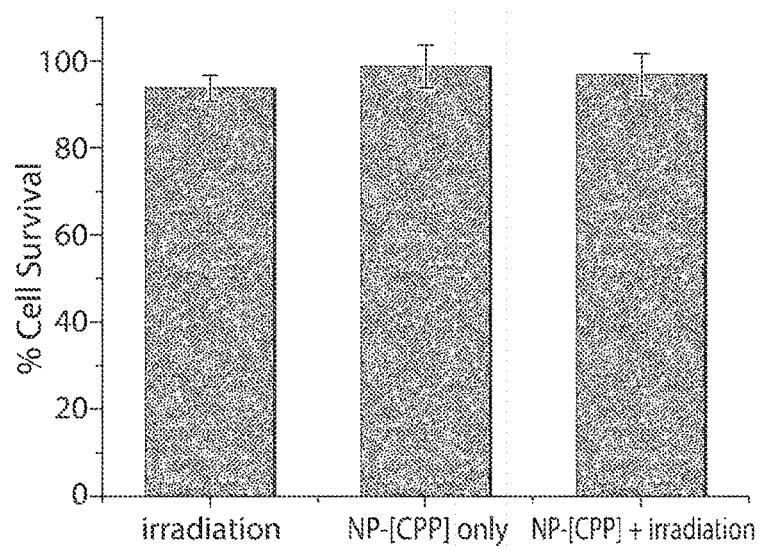
FIG. 7 illustrate survival rates of cells, in accordance with yet another set of embodiments.

FIG. 7 shows survival rates determined by MTS assay of HUVECs after irradiation (400 nm at 50 mW/cm$^{-2}$ for 1 min, at the beginning of incubation) and/or overnight incubation with 0.5 mg/mL NP-[CPP]. Data are means+/-SD (n=4).

The safety of the irradiation conditions was further studied in vivo. Under isoflurane anesthesia, the eyes of C57BL/6 mice were irradiated with 400 nm LED for 5 min at 50 mW/cm$^2$. No abnormalities such as corneal clouding or signs of cataracts were observed with a fundus camera (see below) within 48 h after irradiation (FIG. 3). Tissue sections stained with hematoxylin and eosin (H&E) revealed normal histology in irradiated cornea and retina, and no detectable difference between irradiated and non-irradiated eyes. (compare FIGS. 3C and 3D).

FIG. 3 shows murine ocular tissue reaction to 400 nm LED irradiation at 50 mW cm$^{-2}$ for 5 min. FIG. 3A shows a photograph showing clear cornea with unobstructed view of underlying iris. FIG. 3B shows a photograph showing clear cornea and lens with unobstructed view of retina through dilated pupil. FIG. 3C shows a photomicrograph of hematoxylin-eopsin stained section of retina, showing no detectable injury. FIG. 3D shows a photomicrograph of hematoxylin-eopsin stained section of cornea, showing no detectable injury.

Example 5

Light-triggered targeting in vivo in mouse CNV model. The laser-induced mouse model of CNV was used to investigate nanoparticle phototargeting in vivo. In brief, in this example, CNV was induced by laser photocoagulation-induced (532 nm, 0.24 W, 0.07 s) rupture of Bruch's membrane of C57BL/6 mice. Four laser burns indicated by the development of vapor bubbles in Bruch's membrane were induced per eye around the optic disc (approximately 0.5 to 1 mm from the optic nerve). Fundus fluorescein angiography (FA) was used to monitor the development of the vascularity associated with CNV.

Groups of mice with induced CNV were injected intravenously (IV) with 200 μL (5 mg/mL) of AMF-PEG-PLA-labeled nanoparticles in four groups: NP-AMF, NP-AMF-CPP, NP-AMF-[CPP], and NP-AMF-[CPP] with irradiation (NP-AMF-[CPP]+hv) where irradiation was performed immediately (30 s) after IV injection. Thirty seconds after IV injection, the fluorescent nanoparticles were observed in the mouse fundus by FA and the intense fluorescence persisted for 5 min. Fluorescence was brightest during the first 4 minutes after IV injection of nanoparticles, in both retinal blood vessels and laser-induced lesions (FIG. 8). Fluorescence in the retinal blood vessels was still visible in vivo 8 h after nanoparticle injection, but not 24 h after injection. Microscopy of the flat-mounted retina 24 h after IV injection revealed no fluorescence in the retinal vessels.

Figure 8A:
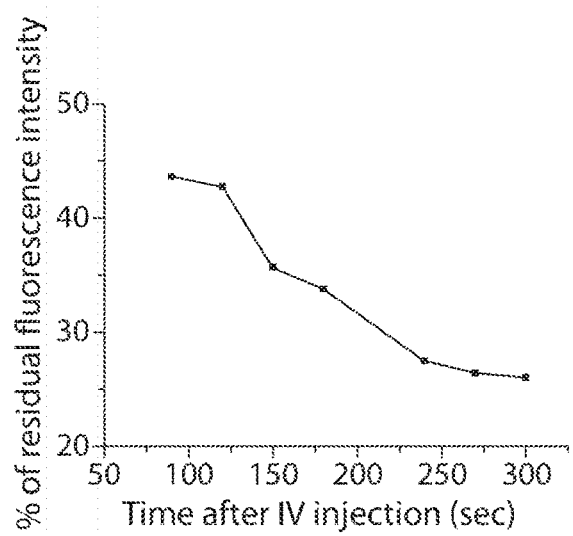
FIGS. 8A-8B illustrate treatment of retinal blood vessels, in still another set of embodiments.
Figure 8B:
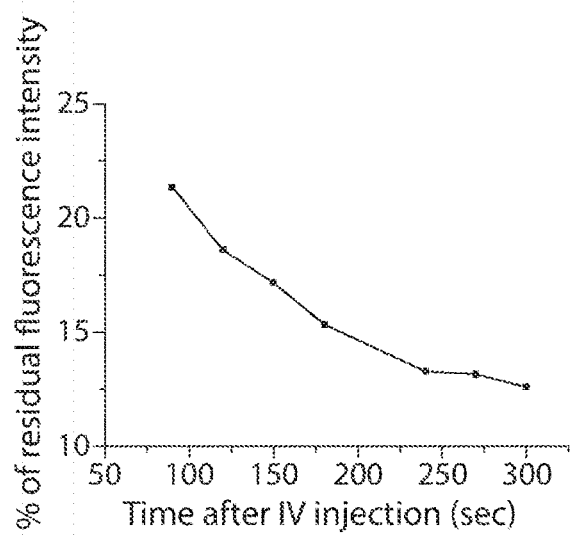

FIG. 8 shows quantification of the average fluorescence intensity in (FIG. 8A) retinal blood vessels and (FIG. 8B) laser-induced lesions, after IV injections of fluorescently labeled nanoparticles.

To evaluate the accumulation of nanoparticles in the neo-formed CNV lesions, mice were euthanized 24 h after nanoparticle injection, and their eyes were enucleated for laser scanning confocal microscopy of flat-mounted choroids (FIG. 4). Higher fluorescence intensity was observed in the eyes of mice in the NP-[CPP]+hv group than in the others (NP, NP-CPP and NP-[CPP] without irradiation), confirming that photo-targeting enhanced nanoparticle accumulation in the CNV areas. Minimal fluorescence was observed in choroidal flat-mounts of healthy eyes of mice injected with nanoparticles, suggesting that the leaky vasculature in CNV plays an important role in nanoparticle accumulation.

Biodistribution of nanoparticles was determined by measuring the fluorescence intensity in organs harvested 24 h after nanoparticle injection. When AMF was extracted from the same organs and the fluorescent content was measured (FIG. 9A), it was found in all organs, with the greatest concentration in liver. Fluorescence was undetectable by this approach in all choroids, even though fluorescence was seen on microscopy, possibly due to the small amounts of material involved (the entire choroid weighed ~1 mg). Therefore, the mean fluorescence intensity in the choroids (from microscopy, FIG. 4B) was used as the metric for AMF accumulation in the eye. It was found that the ratio of AMF accumulation in the eye to that in other organs in the NP-AMF-[CPP]+hv group was roughly twice (1.7 to 2.4 fold, depending on the organ) that in the NP-AMF-[CPP] group (FIG. 9B).

Figure 4A:
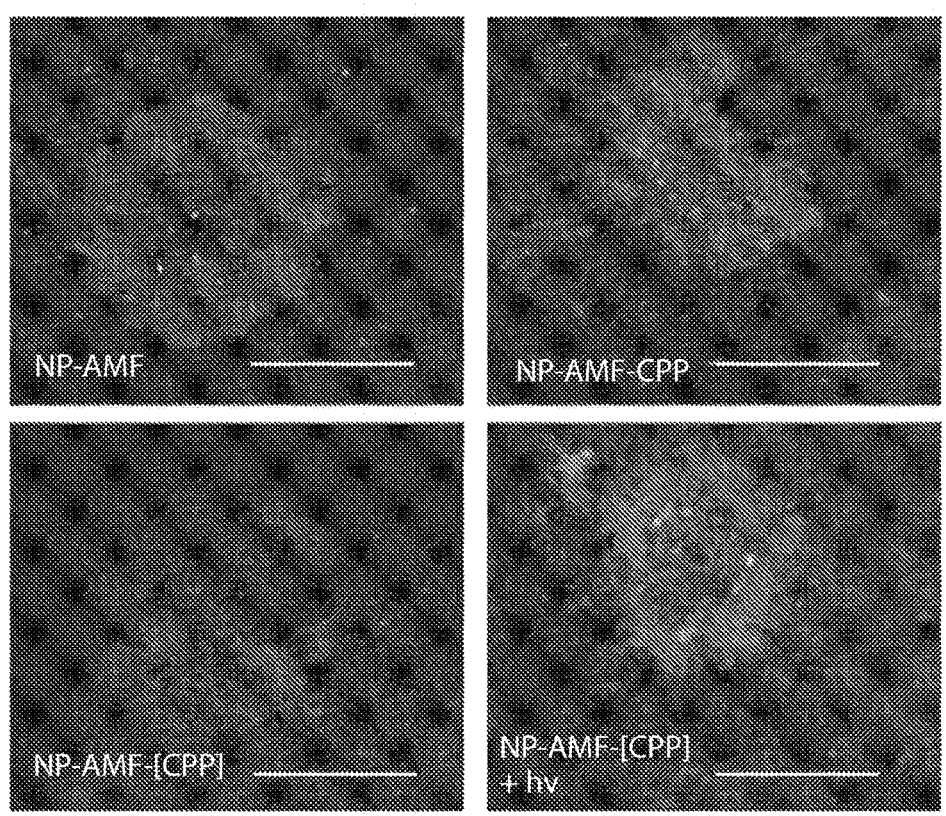
FIGS. 4A-4B illustrate light-triggered targeting, according to still another set of embodiments.
Figure 4B:
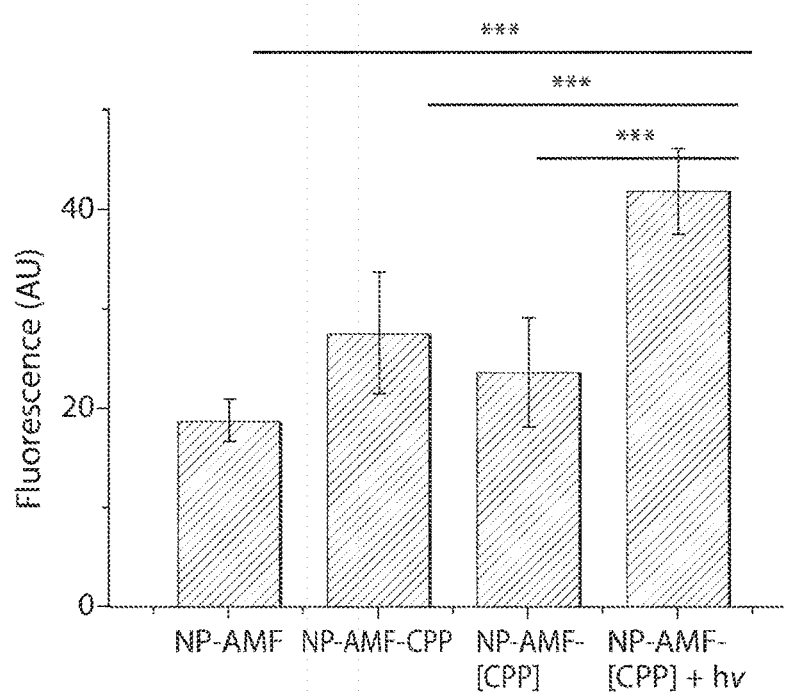

FIG. 4 shows light-triggered targeting of CNV in vivo. FIG. 4A shows representative (of 8) images of blood vessels on a flat-mounted choroid 24 hours after injection with NP-AMF with or without 400 nm LED irradiation at 50 mW cm$^{-2}$ for 3 min. The scale bar is 100 micrometers. FIG. 4B shows quantification of the intensity of fluorescent neovessels from images in FIG. 4A, normalized by the lesion size. Data are means+/−SD (n=8) ***P<0.001.

Figure 9A:
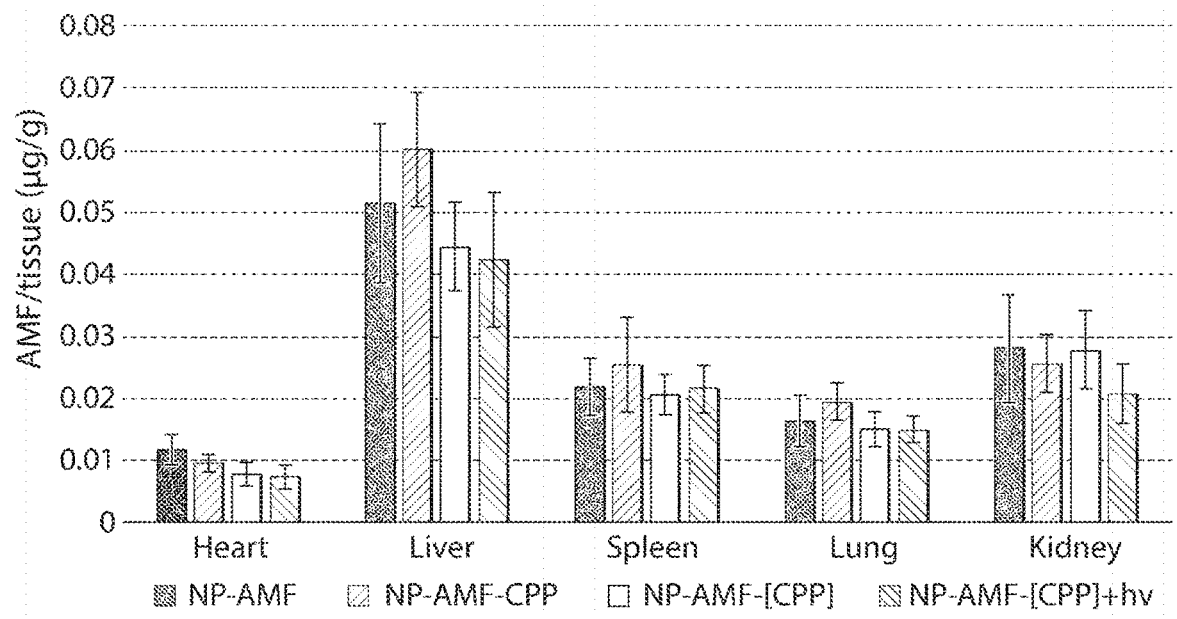
FIGS. 9A-9B illustrate particle distributions, in another set of embodiments of the invention.
Figure 9B:
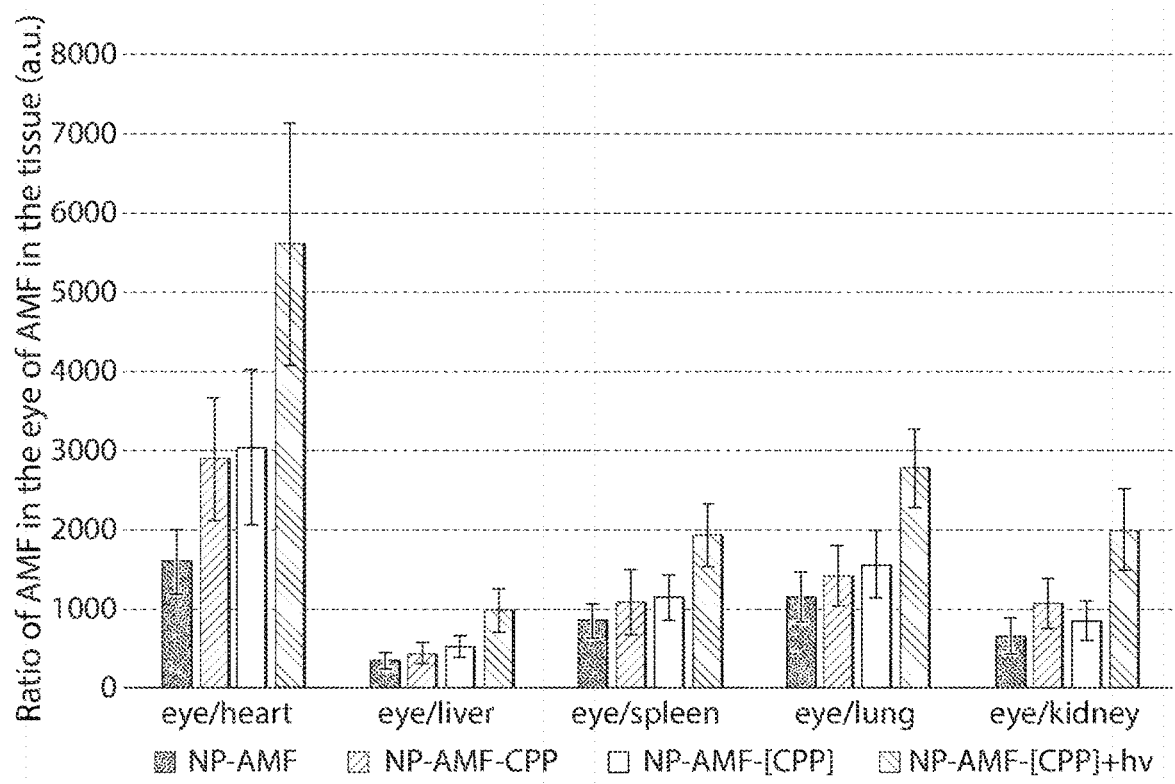
Figure 10:
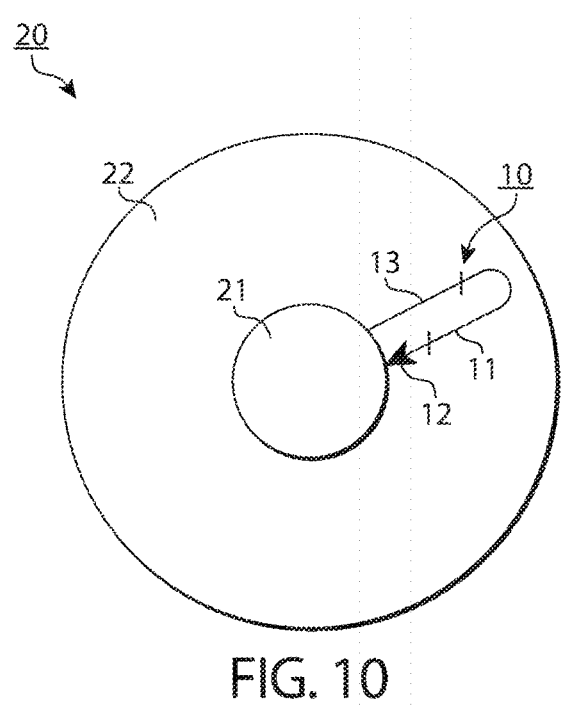
FIG. 10 is a schematic illustration of another embodiment of the invention.

FIG. 9 shows biodistribution of injected formulations in mice 24 h after intravenous injection. FIG. 9A shows the effect of treatment group on AMF per gram of tissue harvested. FIG. 9B shows the effect of treatment group on ratio of AMF in the eye (from data in FIG. 4B) to AMF in tissue (data in FIG. 9A). Data are means+/−SD (n=4).

Example 6

Therapeutic effects of phototriggered activation of nanoparticles in CNV. The mouse model of laser-induced choroidal neovascularization mimics the neovascular aspect of wet AMD, and has been used extensively in studies of that disease. However, unlike the chronic development of wet AMD in human, the laser-induced mouse CNV model is acute—the optimum time point to assess neovessels in this model is between day 7 and day 14. After 14 to 21 days, spontaneous regression begins and lesion size decreases. The dosing regimen in this example was determined accordingly: treatment was initiated on day 7 when the lesions had formed, and its effects were assessed before spontaneous regression would begin on day 14.

The drug doxorubicin (doxo), which inhibits CNV when injected intraocularly, was encapsulated in the nanoparticles by a one-step process where the drug was co-dissolved with polymers in an organic solvent and under reduced pressure formed a thin-film, which was then hydrated to form nanoparticles. The drug loading was 0.2+/−0.03 mg of doxorubicin per 10 mg of nanoparticles; the loading efficiency was 39.0+/−4.1%. In vitro release of doxorubicin was assessed by dialyzing 500 microliters of NP-[CPP] encapsulating doxorubicin (NP-[CPP]-doxo) against 14 mL of phosphate-buffered saline (PBS). 91.3+/−2.0% of doxorubicin was released in the first 48 hours, and release was complete by 7 days (FIG. 5A).

In the in vivo therapeutic study, 200 microliters of PBS containing 1 mg of NP-[CPP]-doxo encapsulating 0.02 mg doxorubicin were injected via tail vein one week after photocoagulation (day 1 of treatment), and additional injections were given on day 3 and day 5. (Given the release kinetics of the nanoparticles, this would constitute ~1 week of treatment.) Thirty seconds after nanoparticle injection, the mouse eyes were irradiated with a 400 nm LED for 3 min at 50 mW/cm$^2$ (NP-[CPP]-doxo+hv). Analogous experiments were done with PBS, free drug, NP-doxo, and non-irradiated NP-[CPP]-doxo. (The three drug-loaded groups contained equal doses of doxorubicin.) On day 7, mice were euthanized, the size of CNV lesions was assessed by fluorescent imaging of choroidal flat-mounts stained with isolectin GS-IB4 (which labels endothelial cells). Mice treated with NP-[CPP]-doxo+hv showed a 46.1% reduction in neovessel area compared to the group treated with PBS. The free doxorubicin group and that with NP-[CPP]-doxo without irradiation showed 26.8% and 24.0% reduction in neovessel area respectively, approximately half of the inhibitory effects of NP-[CPP]-doxo with irradiation (FIG. 5).

Figure 5A:
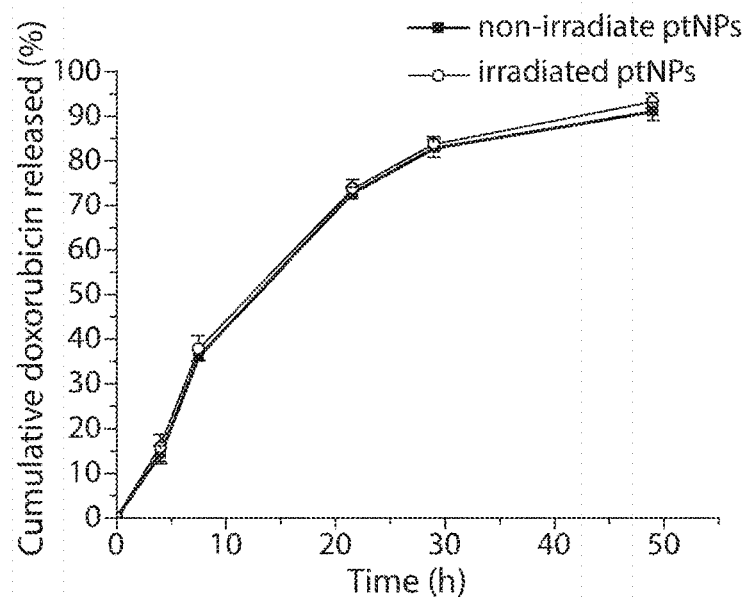
FIGS. 5A-5B illustrate treatment using particles in accordance with another set of embodiments.
Figure 5B:
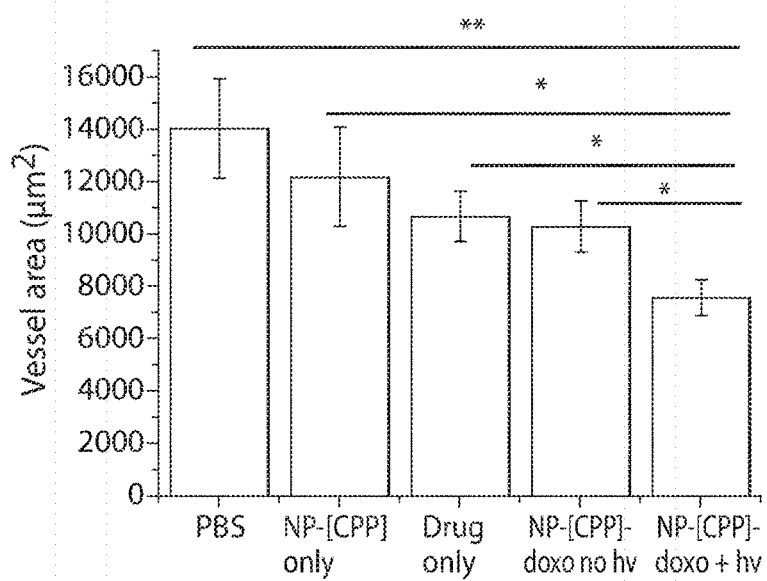

FIG. 5 shows treatment with NP-[CPP]-doxo in mouse CNV model. FIG. 5A shows cumulative doxorubicin release (as % of total amount loaded) from NP-[CPP]-doxo at 37° C. in vitro by dialysis, with or without irradiation (400 nm LED for 1 min at 50 mW/cm$^2$) at t=0. Data are means+/−SD (n=4). FIG. 5B shows mean CNV lesion area from laser-induced CNV mice treated with PBS, NP-[CPP], doxo, NP-[CPP]-doxo, and NP-[CPP]-doxo with irradiation. Error bars show standard error of the mean. n=23-28 lesions. *$P<0.05$, ** $P<0.005$.

Tissue reaction. Histological study of organs including the heart, kidney and spleen revealed normal histology and did not show any detectable differences between the treated groups and saline-injected animals. In all groups including saline-injected controls, there were foci of mild acute interstitial inflammation in predominantly normal lungs and of chronic inflammation in the liver. As these changes were not exclusive to the treated groups but were seen in the untreated controls, the nanoparticles are an unlikely etiology. The histologic changes in the lung and liver were seen across all groups and are attributed to infection/inflammation related to housed animals.

Accordingly, these examples illustrate an intravenously injected, photo-targeted treatment regimen for CNV and demonstrated its efficacy in the standard mouse CNV model. It was shown that phototargeting can enhance nanoparticle accumulation in the abnormal vessels in CNV, and can significantly enhance treatment. Notably, the inhibition effect of NP-[CPP]-doxo plus irradiation on CNV growth was comparable to locally-administered drug formulations. The intensity and duration of irradiation used in these experiments did not cause damage to the mouse eyes, and NP-[CPP]-doxo did not cause tissue toxicity.

Example 7

This example illustrates various methods and materials used in the above examples.

Synthesis of polymer-peptide conjugates. To synthesize [CPP]-PEG-PLA, 20 mg of maleimide-PEG-PLA and 10 mg of [CPP] were dissolved in 500 microliters DMSO-d$_6$. The mixture was shaken at room temperature and $^1$H NMR was used to monitor the reaction until the methine proton peak from maleimide disappeared. The reaction mixture was diluted with H$_2$O, placed in a Spectra/Por® 6 dialysis membrane (molecular weight cutoff, MWCO: 3500 Da) and dialyzed against 4 changes of 2 L of distilled water at 4° C. After 2 days of dialysis, the dialyzed solution was lyophilized.

To synthesize AMF-PEG-PLA, 20 mg of NHS-PEG-PLA and 4 mg of 4'-(aminomethyl)fluorescein (ThermoFisher Scientific) were dissolved in 300 microliters DMSO. 0.6 microliters of DIPEA was added, and the mixture was shaken for 5 hours at room temperature. The mixture was diluted with H$_2$O, then dialyzed (as above) and lyophilized.

Preparation of polymeric nanoparticles. To prepare NP-[CPP], [CPP]-PEG-PLA (2.0 mg) and PLA-mPEG (8.0 mg) were co-dissolved in 5 mL of chloroform. Rotary evaporation was used to slowly evaporate the solvent at 45° C. The dried polymer film was hydrated with 2 mL of PBS at 60° C. For other nanoparticles, the same procedure was used except that different compounds were added for each type of nanoparticle. For NP: mPEG-PLA (10.0 mg); NP-CPP: CPP-PEG-PLA (2.0 mg) and mPEG-PLA (8.0 mg). For NP-AMF: AMF-PEG-PLA (1.0 mg) and mPEG-PLA (9.0 mg). For NP-AMF-[CPP]: [CPP]-PEG-PLA (2.0 mg), AMF-PEG-PLA (1.0 mg) and mPEG-PLA (7.0 mg). For NP-AMF-CPP: CPP-PEG-PLA (2.0 mg), AMF-PEG-PLA (1.0 mg) and mPEG-PLA (7.0 mg).

Characterization of micelles by transmission electron microscopy: a 10 microliter aliquot of the nanoparticle solution was deposited on a copper grid coated by a carbon film. After 2 min, excess solution was blotted by a filter paper. The sample was dried at room temperature and then imaged on a Tecnai G$^2$ Spirit BioTWIN transmission electron microscope (FEI company, OR, USA) operating at 80 kV.

Characterization of nanoparticles by dynamic light scattering: the size of nanoparticles was measured with a Delsa Nano C particle analyzer (Beckman Coulter, Calif., USA). A nanoparticle solution (100 microliters) was put into a disposable cuvette (Eppendorf UVette) and tested at 25° C. with the accumulation times of 70. Each sample was tested at least 3 times. The hydrodynamic diameter was calculated by averaging the repeated measurements of diameters.

Photocleavage of DEACM-OH from NP-[CPP]. To measure the rate of phototriggered release of DEACM from NP-[CPP], a quartz cuvette containing 1 mL of NP-[CPP] solution (0.5 mg/mL$^{-1}$) was irradiated under an 11-mm LED light (400 nm) collimator with a multi-channel Universal LED controller (Mightex Systems, Calif., USA). The temperature of the solution was controlled at 37° C. in a t50/Eclipse cuvette holder with a TC 125 temperature controller (Quantum Northwest, Wash., USA). The LED irradiance was measured with a PM100USB Power and Energy Meter (ThorLabs, N.J., USA). At each irradiation time point, the solution was put in an Amicon® Ultra centrifugal filter (MWCO: 50000 Da) and centrifuged at 4000 rpm for 20 min. The filtrate was analyzed by RP-HPLC ($\lambda$, lambda=390 nm) with a Poroshell 120 EC-C18 column.

Flow cytometry. Cells were cultured in cell growth media in a humidified atmosphere with 5% CO$_2$ at 37° C. in a 48-well plate at a density of 40,000 cells per well. After overnight incubation, the growth media was replaced with fresh media containing different nanoparticles at a concentration of 0.4 mg mL$^{-1}$, in the following groups: NP-AMF, NP-AMF-CPP, NP-AMF-[CPP], and NP-AMF-[CPP] with irradiation (400 nm, 50 mW cm$^{-2}$, 1 min). After 30 min of incubation at 37° C., the cells were washed with PBS twice and detached with 150 microliters of 0.25% Trypsin-EDTA solution. The cells were suspended with 350 microliters of trypsin neutralizing solution (TNS) and transferred into BD Falcon round-bottom tube (BD Bioscience, N.J., USA). The flow cytometry was run on BD LSR Fortessa cell analyzer (BD Bioscience, N.J., USA).

Confocal laser scanning microscopy. Cells were seeded on a 35-mm glass bottom dish with collagen coating (MatTek Corporation, Mass., USA) at a density of 250,000 cells per well. After overnight incubation, the growth media was replaced with the fresh media containing different nanoparticles at a concentration of 0.4 mg mL$^{-1}$, in the following groups: NP-AMF, NP-AMF-CPP, NP-AMF-[CPP], and NP-AMF-[CPP] with irradiation (400 nm, 50 mW cm$^{-2}$, 1 min). After 30 min of incubation at 37° C., the cells were washed with PBS twice and imaged by confocal microscopy (488 nm, Zeiss LSM 710).

Cytotoxicity analysis. Cell viabilities were evaluated with an assay of mitochondrial metabolic activity (the MTS assay), CellTiter 96 Aqueous One Solution Cell Proliferation Assay (Promega Corp.), that uses a tetrazolium compound [3-(4,5-dimethyl-2-yl)-5-(3-carboxymethoxyphenyl)-2-(4-sulfophenyl)-2H-tetrazolium, inner salt (MTS)] and an electron coupling reagent (phenazine ethosulfate). HUVEC were incubated with CellTiter 96 AQueous One Solution for 120 min at 37° C. The absorbance of the culture medium at 490 nm was immediately recorded with a 96-well plate reader. The quantity of formazan product (converted from tetrazole) as measured by the absorbance at 490 nm is directly proportional to cell metabolic activity in culture.

Loading efficiency of doxorubicin in NP-[CPP]. To prepare NP-[CPP]-doxo, [CPP]-PEG-PLA (2.0 mg), mPEG-PLA (8.0 mg) and doxorubicin (0.5 mg) were co-dissolved in 5 mL of chloroform. Rotary evaporation at 45° C. was used to slowly remove the solvent. The dried polymer film was hydrated with 2 mL of PBS at 60° C.

The NP-[CPP]-doxo was centrifuged at 4000 rpm for 10 min to remove aggregated un-encapsulated doxorubicin. To determine NP doxorubicin content, an aliquot of doxo-containing micelles was then lyophilized and dissolved in DMSO. High-performance liquid chromatography (HPLC) analysis of the diluted solution was measured and compared to standard curves for doxorubicin.

In vitro doxorubicin release. Doxorubicin release experiments were performed by placing 500 microliters of NP-[CPP]-doxo into a Slide-A-Lyzer MINI dialysis device (Thermo Scientific) with a 10,000 molecular weight cut-off. The sample was dialyzed against 14 mL PBS and incubated at 37° C. on a platform shaker (New Brunswick Innova 40; Eppendorf) at 200 rpm. At predetermined time points, the dialysis solution (release medium) was exchanged with fresh PBS. To determine doxorubicin release from irradiated NP-[CPP], nanoparticles were irradiated by 400 nm LED for 1 min at 50 mW/cm$^2$ at the beginning of the in vitro release study. The doxorubicin concentration in aliquots of release media was determined by HPLC ($\lambda$, lambda=233 nm).

Animal studies. Healthy adult female C57BL/6 mice (6-8 weeks) weighing 19 to 21 g were purchased from Charles River (Wilmington, Mass., USA). Experiments were carried out in accordance with protocols approved by Boston Children's Hospital Institutional Animal Care and Use Committee. The induction of laser-induced choroidal neovascularization was performed according to previously established protocols. Mice were anesthetized with a mixture of ketamine (100 mg/kg, IP) and xylazine (6 mg/kg, IP). Their pupils were then dilated with a topical drop of Cyclomydril® (Alcon Laboratories, Fort Worth, Tex.). After pupils were dilated (3-5 min), the mouse eyes were hydrated with GenTeal® eye drops. A Micron IV imaging guided laser system (Phoenix Research Labs, Pleasanton, Calif.) was used to generate four laser burns (power 0.24 watts, duration 0.07 s) in each eye, in a pattern surrounding and of equal distance to the optic nerve head, while avoiding major retinal vessels. The four laser burns were imaged with the camera in Micron IV imaging system. The formation of CNV lesions was monitored by injecting anesthetized mice intraperitoneally with Fluorescein AK-FLUOR® (100 mg/ml, Akorn, Lake Forest, Ill., USA) at 100 microgram/g (body weight) and taking fluorescent fundus images with a Micron IV imaging system.

Fluorescence imaging of flat-mounted choroids. One week after photocoagulation, mice were anesthetized with isoflurane, and their eyes were dilated with a drop of Cyclomydril®. 3 min later, AMF-labeled nanoparticles were injected via tail vein. For mice that were treated with nanoparticles and irradiation, the mouse eyes were irradiated by 400 nm LED for 3 min at 50 mW/cm$^2$ immediately after (~30 sec) tail vein injection. GenTeal® eye drops were then applied to hydrate the eyes. A Micron IV imaging system was used to monitor the distribution of AMF-labeled nanoparticles in the mouse fundus. 24 hours later, mice were euthanized, their eyes were enucleated and cleaned in PBS. Eyes were then fixed with 4% paraformaldehyde for 1 hour at room temperature, and rinsed with PBS afterwards. Under an illuminated microscope, the cornea and lens were dissected, then the entire retina was removed from the eyeball. The retina was carefully separated from the choroid, and four cuts were made to easily flatten the choroid onto a slide. After the choroids were mounted with Invitrogen antifade reagent, the slides were imaged by confocal microscopy (488 nm, Zeiss LSM 710). The images were digitized with a three-color camera. Volocity software (PerkinElmer, Mass., USA) was used to quantify the average intensity of fluorescence in each CNV lesion.

Biodistrubition study. Mice were euthanized 24 h after injection of AMF-labelled nanoparticles and their organs were collected. Organs were weighed and sonicated in 500 microliters 5% Triton X-100 solution (Sigma Aldrich) on ice for 2 min, then the same volume of methanol was added to extract the AMF and another 2 min of sonication was performed. Mixtures underwent mechanical agitation for 2 min and were then centrifuged at 14,000 rpm for 15 min (Microfuge 22R Centrifuge, Beckman Coulter, Calif., USA). To determine the content of AMF in each tissue homogenate sample, 800 microliters of the supernatant solution was transferred into a cuvette and analyzed by a fluorescence spectrometer (Agilent, Calif., USA). Tissue samples from untreated mice were measured as controls for autofluorescence, which was subtracted from the fluorescence intensity of the experimental groups. The data were divided by tissue mass (microgram/g).

Histology. For ocular histology studies, enucleated eyes were embedded in OCT compound in a cryomold with its optic nerve-pupil axis oriented horizontally and frozen with liquid nitrogen vapor. 8-micrometer cryosections of the tissue were stained with hematoxylin and eosin and assessed by light microscopy. Eyes from normal untreated mice were used as controls.

For organ histology studies, mice were euthanized after one week of treatment with free drug (doxorubicin), nanoparticles without drug and nanoparticles with doxorubicin. Mice injected with PBS were used as controls. Organs were harvested, fixed with 10% formalin, embedded in paraffin, sectioned, and stained with hematoxylin and eosin. Histologic assessment by light microscopy was performed by a pathologist in a blinded fashion.

Analysis of the CNV neovessel area. Mouse choroids were stained with isolectin GS-IB$_4$, Alexa fluor™ 594 conjugate (Invitrogen), and images were obtained by a Zeiss Observer.Z1 fluorescence microscope. Images were digitized with a digital camera. ImageJ software (NIH, USA) was used to measure the total area (in micrometers$^2$) of CNV associated with each laser burn by an observer (Y.W.) who was blinded to the nature of the individual images. A calibration image was taken from a slide with a grating of known size. An established and constant threshold in pixels (corresponding to threshold fluorescence) was used to outline the fluorescent blood vessels and quantify the area of neovascularization. A lesion was excluded if one of the following conditions occurred, according to previously reported protocols: (1) there was choroidal hemorrhage; (2) the lesion was linear instead of circular; (3) there was fusion of two or more lesions; (4) the lesion was the only lesion in an eye; (5) the area of the lesion was more than 5-fold larger than the next biggest lesion in the same eye, or less than ⅕ the area of the next smallest lesion in the eye.

Statistical analysis. Statistical analysis was conducted using OriginPro software (version 8, OriginLab). All p values were calculated by the unpaired t-test, p<0.05 was considered statistically significant.

Materials. Chemicals were purchased from Sigma-Aldrich (Missouri, USA) and used without further purification unless otherwise stated. Poly(D,L-lactic acid)(2000)-poly(ethylene oxide)(3000)-N-hydroxysuccinimide (PLA-PEG-NHS) and PLA(2000)-methoxy PEG (mPEG, 2000) (PLA-mPEG) were ordered from Advanced Polymer Materials (Montreal, Canada). 7-diethylamino-4-hydroxymethylcoumarin was bought from INDOFINE Chemical Company (New Jersey, USA). The CPP (amino acid sequence Ac-CGGFRKKRRQRRR) (SEQ ID NO: 1) was purchased from GL Biochem Shanghai LTD (Shanghai, China). Human umbilical vein endothelial cells (HUVECs) and endothelial cell growth media kits (EGMTM-2 BulletKit, Catalog #CC-3162) were purchased from Lonza (New Jersey, USA). The CellTiter® 96 Aqueous One Solution Cell Proliferation Assay solution was purchased from Promega (Wisconsin, USA). Other cell culture agents were purchased from Life Technologies (Now York, USA).

Production of doxorubicin free-base. 10 mg of doxorubicin hydrochloride salt was dissolved in $H_2O$. 10 microliters of trimethylamine was added to the solution under mechanical agitation. The mixture was centrifuged at 4500 rpm for 15 mins, and the precipitate was washed with water 3 times, then dried under vacuum.

Synthesis of caged peptide ([CPP]). (7-(diethylamino)-2-oxo-2H-chromen-4-yl)methyl (4-nitrophenyl) carbonate (DEACM-carbonate) was synthesized following as reported.[1] DEACM-carbonate was then reacted with the CPP as follows: 56.7 mg of DEACM-carbonate (0.137 mmol) was dissolved in 600 microliters of DCM. N,N-Diisopropylethylamine (DIPEA, 23.94 microliters, 0.137 mmol) and 60 mg of CPP (0.034 mmol) dissolved in 400 microliters of DMF. DEACM-carbonate solution was then added dropwise to the CPP solution. The mixture underwent mechanical agitation for 24 hours, then was separated by HPLC (C4 column, "H8" 214TP52, 2.1×150 mm, from Vydac, Hesperia, Calif.). The mobile phase consisted of solvent A (0.05% TFA in $H_2O$) and B (0.043% TFA, 80% ACN in $H_2O$). 10% solvent B was used as the mobile phase from 0 to 10 min, then the percentage of B in the mobile phase was linearly increased to 100% from 10 to 55 min. The flow rate was 0.3 mL/min.

Example 8

Although photo-toxicity was not detected, 400 nm (blue light) is known to be in the high photoreceptor sensitivity region. This example investigated if irradiation with blue LED light at lower intensity could lead to similar levels of NP accumulation in the CNV lesions.

Groups of mice with induced CNV were injected intravenously with 200 microliters (5 mg/mL) of NP-AMF-[CPP] and irradiation was performed immediately (30 s) after IV injection.

The group of mice that received irradiation at 5 $mW/cm^2$ for 10 min had similar NP accumulation in the lesions as those that received 50 $mW/cm^2$ for 3 min, which was higher than the accumulation in the groups that underwent irradiation at 1 $mW/cm^2$ for 10 min, 10 $mW/cm^2$ for 5 min or 50 $mW/cm^2$ for 1 min.

The phototargeted accumulation of NPs in the CNV lesions may be dependent on the pharmacokinetics of NPs in the choroidal neovessels, as well as the passive accumulation of NPs in the CNV area due to EPR-like effect. These data suggested that low irradiation intensity (1 $mW/cm^2$) was not sufficient for phototargeting, and neither was short irradiation duration (1 min). Irradiation at higher intensity (50 $mW/cm^2$) for intermediate durations (3 min) or at intermediate intensity (5 $mW/cm^2$) for longer durations (10 min) resulted in efficient phototargeting, probably because the former regimen was able to activate almost all the NPs in the CNV area during the first three minutes after NP injection when NP concentration in the vessels was highest, while the latter was able to capture a broader range of the pharmacokinetic curve.

Figure 11:
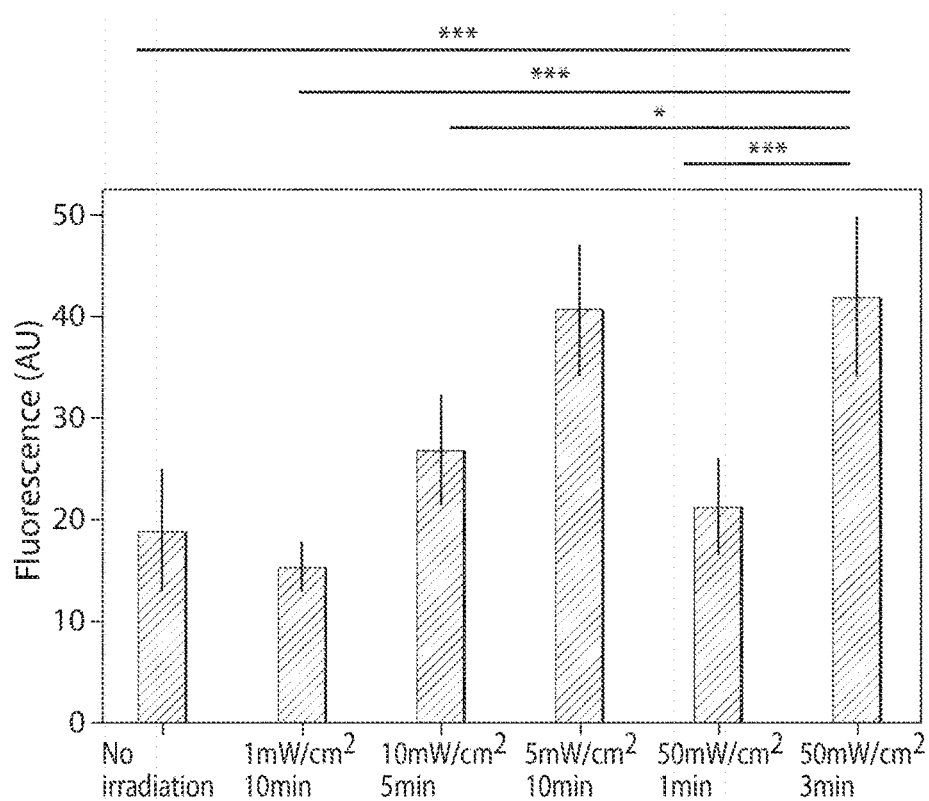
FIG. 11 illustrates phototargeting of nanoparticles, in one embodiment of the invention.

FIG. 11 shows quantification of the intensity of fluorescent neovessels, normalized by the lesion size. Data were means+/−SD (n=8 lesions) *P<0.05, *** P<0.001 (unpaired t-test).

Example 9

The composition of the NP building blocks, di-block copolymer PEG-PLA, may determine the size, morphology, and/or surface properties of the NP. This example investigated if different compositions of PEG-PLA could be used to formulate targeting NPs.

To synthesize CPP-PEG(5K)-PLA(10K), 20 mg of maleimide-PEG(5K)-PLA(10K) and 10 mg of CPP were dissolved in 500 microliters DMSO-$d_6$. The mixture was shaken at room temperature and $^1H$ NMR was used to monitor the reaction until the methine proton peak from maleimide disappeared. The reaction mixture was diluted with $H_2O$, placed in a Spectra/Por® 6 dialysis membrane (molecular weight cutoff, MWCO: 3500 Da) and dialyzed against 4 changes of 2 L of distilled water at 4° C. After 2 days of dialysis, the dialyzed solution was lyophilized.

To prepare NP-AMF-CPP, CPP-PEG-PLA (2.0 mg), AMF-PEG-PLA (1.0 mg) and mPEG-PLA (7.0 mg) were dissolved in 0.5 mL THF, then the polymer solution was added drop-wise to 5 mL $H_2O$ under stirring. After 4 hr stirring at room temperature, the NP solution was washed three times with PBS and concentrated using Amicon® Ultra centrifugal filter (MWCO: 10000 Da) at 3082×g for 20 min.

The resulting NPs had a hydrodynamic diameter of 37+/−4 nm (means+/−SD; n=4), as measured by DLS. Cellular uptake of NPs by human umbilical vein endothelial cells (HUVECs) was studied by flow cytometry. HUVEC uptake of NP-CPP(5K/10K) was much lower than that of NP-CPP(3K/2K), which may be because the longer PLA block led to the formation of vesicles and compound micelles, instead of only the spherical micelles in the case of PEG(3K)-PLA(2K), and consequently a lower percentage of CPP on the NP surface.

These results suggest that in order to achieve CPP-mediated cellular uptake of NPs, sufficient CPP density on the NP surface may be important, which requires that NPs have a simple spherical micellar structure, or that other modifications (such as higher CPP concentration) be made in the formulation strategy.

Figure 12:
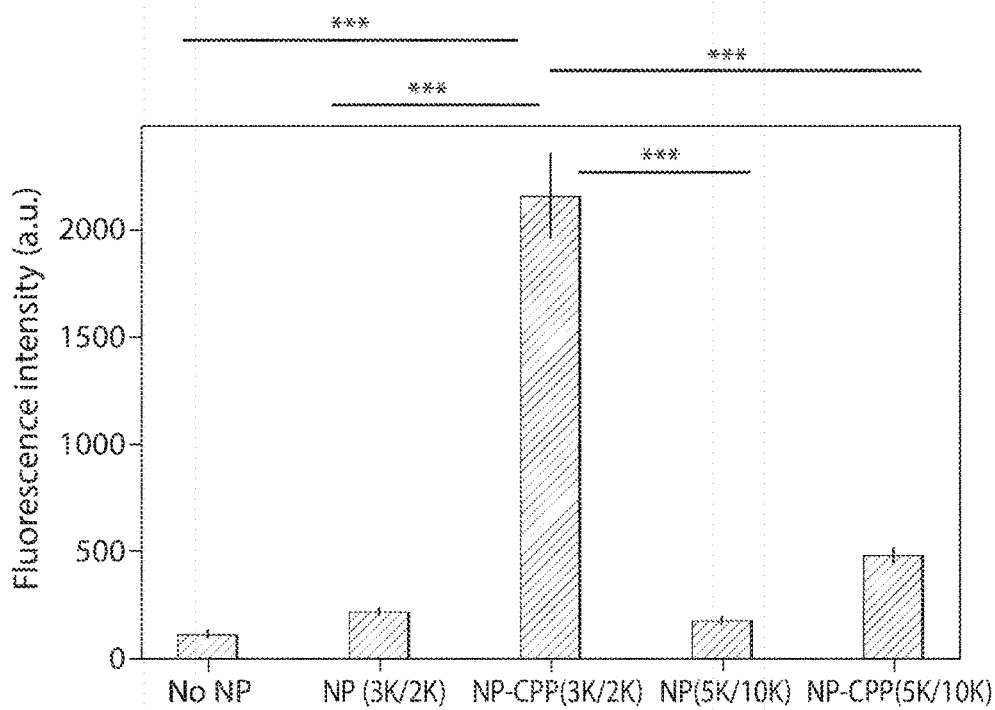
FIG. 12 illustrates uptake of nanoparticles, in another embodiment of the invention.

FIG. 12 shows quantification (mean of four median values of fluorescence intensity) of flow cytometric analyses of HUVEC uptake of nanoparticles. Data are means+/−SD (n=4 independent experiments). ***P<0.001 (unpaired t-test).

Example 10

It may be desirable to design NPs that respond to longer wavelength of light where mammalian retinal photosensitivity is lower, and that have improved uncaging efficiency so that shorter duration or lower intensity of light is required. This example thus illustrates designed NPs that have been labeled with peptides bound by photocaging groups with a higher molar extinction coefficient (for one-photon excitation) or two-photon cross-section and quantum yield.

Figure 13A:
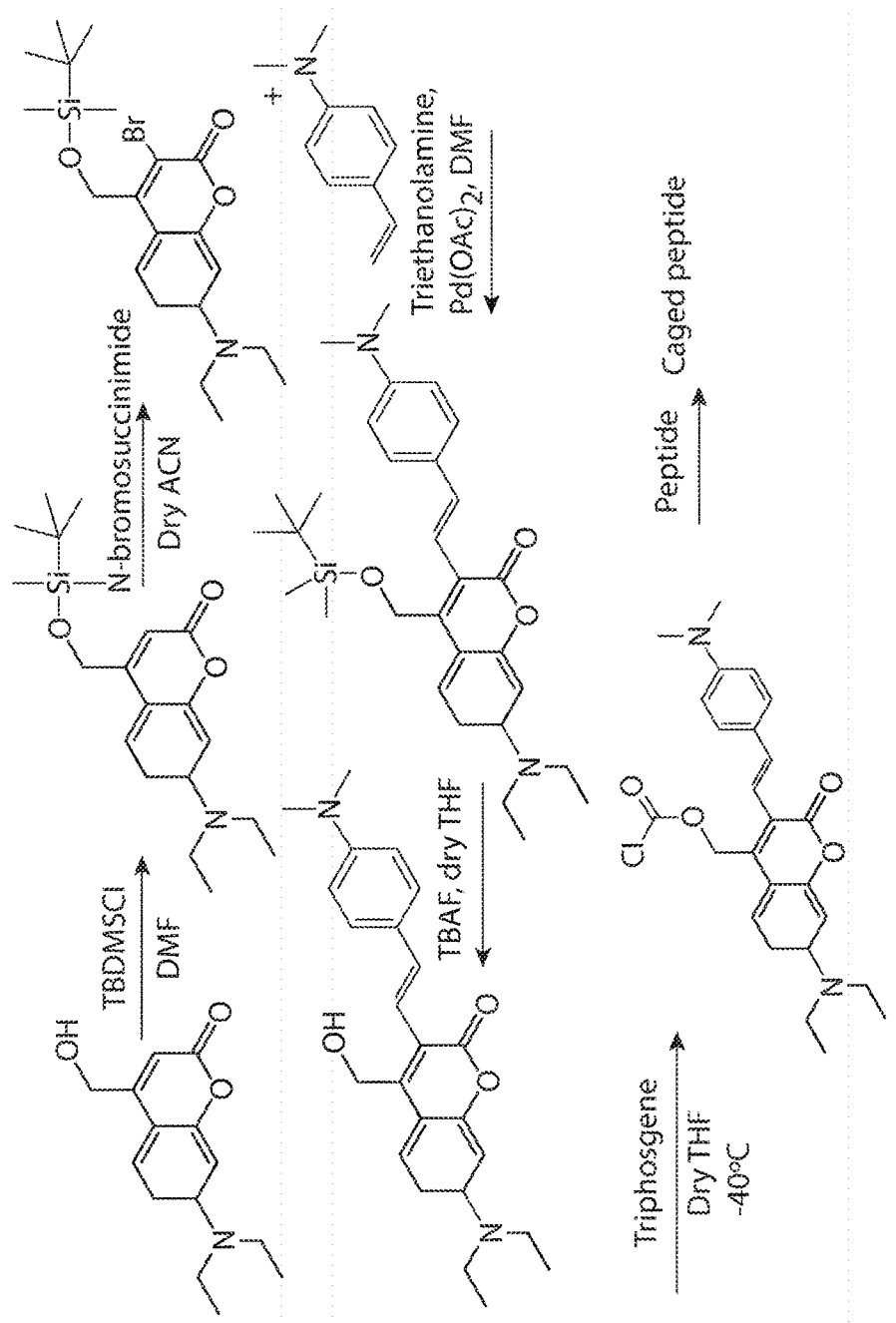
FIGS. 13A-13B illustrate phototargeted nanoparticles in accordance with yet another embodiment of the invention.

The synthetic route of caged-CPP-polymer conjugate is described in FIG. 13A, where a photocaging group was linked to polymer-peptide conjugate using triphosgene. The caged-CPP-polymer was precipitated from reaction mixture by dilution with ether and separated by centrifugation at 10,000× rpm for 10 min. The product was re-dissolved in DCM and precipitated three times to remove impurities. Caged-CPP-polymer and mPEG-PLA was then dissolved in acetonitrile, from which NPs were constructed using film hydration method.

The absorption spectrum of the resulting NPs had a maximum intensity at 445 nm, which changed to 389 nm after irradiation with 470 nm LED light. These phototargeted NPs would allow for efficient phototargeting triggered by longer wavelength (>470 nm with LED light, or >800 nm with two-photon laser), shorter duration and/or lower intensity of light.

Figure 13B:
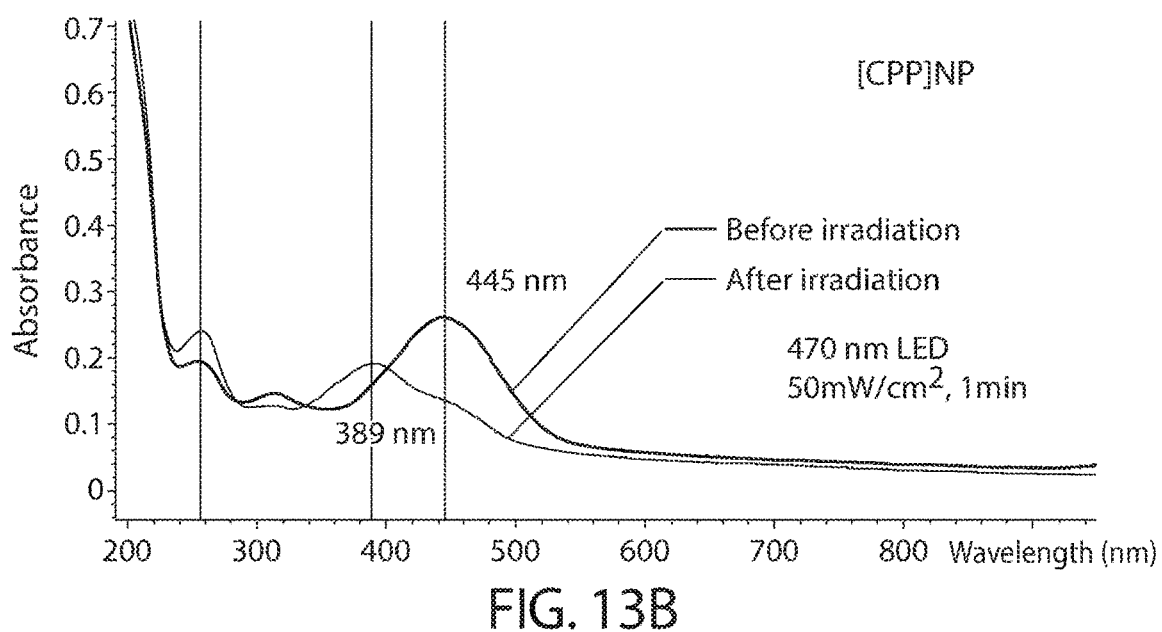

FIG. 13 shows the preparation and characterization of phototargeted nanoparticles. FIG. 13A shows the synthesis of the polymer chain functionalized with caged CPP ([CPP]). FIG. 13B shows UV-Vis absorption spectra of [CPP] NP before and after irradiation with 470 nm LED at 50 mW/cm$^2$ for 1 min.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition, comprising:
a polymeric particle comprising a core and a shell; and
an activatable agent present within the shell, the activatable agent comprising a photocleavable entity comprising 7-(diethylamino)coumarin-4-yl]methyl carboxyl (DEACM) and a targeting moiety comprising CGG-FRKKRRQRRR (SEQ ID NO. 1), wherein the targeting moiety is inhibited from recognizing a target,
wherein a polymer of the polymeric particle comprises a block copolymer of polylactic acid-poly(ethylene glycol) (PLA-PEG).

2. The composition of claim 1, wherein the targeting moiety is inhibited from recognizing a target by the photocleavable entity.

3. The composition of claim 1, wherein the targeting moiety is not present on an outer surface of the particle.

4. The composition of claim 1, wherein the targeting moiety is present at a concentration of at least 20% by mass relative to the volume of the polymeric particle.

5. The composition of claim 1, wherein the activatable agent is covalently bound to at least some of the PLA-PEG block copolymer.

6. The composition of claim 5, wherein the activatable agent is covalently bound to at least some PLA-PEG block copolymer and comprises 20% to 40% by mass of the PLA-PEG block copolymer within the polymeric particle.

7. The composition of claim 1, wherein the activatable agent is covalently bound to PLA via maleimide-thiol coupling.

8. The composition of claim 1, wherein the polymeric particle is a nanoparticle.

9. The composition of claim 8, wherein the nanoparticle comprises a drug.

10. The composition of claim 9, wherein the drug comprise doxorubicin.

11. A method, comprising:

administering, to a subject, a plurality of polymeric nanoparticles such that at least some of the nanoparticles enter systemic circulation within the subject, the polymeric nanoparticles comprising a core, a shell, and an activatable agent present within the shell, the activatable agent comprising a cell-penetrating peptide comprising CGGFRKKRRQRRR (SEQ ID NO. 1) and a photocleavable entity comprising DEACM, wherein the cell-penetrating peptide is inhibited from recognizing a target; and applying light to an eye of the subject, wherein the light cleaves the photocleavable entity to separate at least a portion of the photocleavable entity from the activatable agent, wherein upon separation, the cell-penetrating peptide is able to recognize a target on the surface of a cell, wherein a polymer of the polymeric particle comprises PLA-PEG block copolymer.

12. A method, comprising:

providing a polymeric nanoparticle comprising a core, a shell, and an activatable agent present within the shell, the activatable agent comprising a cell-penetrating peptide comprising CGGFRKKRRQRRR (SEQ ID NO. 1) and a photocleavable entity comprising DEACM, the cell-penetrating peptide being inhibited from recognizing a target; and applying light to the photocleavable entity to cleave the photocleavable entity to separate at least a portion of the photocleavable entity from the activatable agent, wherein upon separation, the cell-penetrating peptide is able to recognize a target on the surface of a cell, wherein a polymer of the polymeric particle comprises PLA-PEG block copolymer.

\* \* \* \* \*